(12) United States Patent
Laux et al.

(10) Patent No.: US 10,283,327 B2
(45) Date of Patent: *May 7, 2019

(54) APPARATUS AND METHODS FOR GENERATING REACTIVE GAS WITH GLOW DISCHARGES

(71) Applicants: The Board of Trustees of the Leland Stanford Junior University, Stanford, CA (US); CentraleSupélec, Gif sur Yvette (FR)

(72) Inventors: Christophe O. Laux, Antony (FR); Johan O. Andreasson, Palo Alto, CA (US); Luke C. Raymond, Stanford, CA (US); Diane Rusterholtz-Duval, Rouen (FR); David Pai, Poitier (FR); Deanna Lacoste, Thuwal (SA); Florent Sainct, Le Cannet (FR); Sebastien Mannai, Anglet (FR); Florian Girschig, Aalborg (DK); Pierpaolo Toniato, Tombolo (IT); Erwan Pannier, Les Martres de Veyre (FR); Augustin Tibère-Inglesse, Le Crès (FR)

(73) Assignees: The Board of Trustees of the Leland Stanford Junior University, Stanford, CA (US); CentraleSupélec, Gif sur Yvette (FR)

( * ) Notice: Subject to any disclaimer, the term of this patent is extended or adjusted under 35 U.S.C. 154(b) by 196 days.

This patent is subject to a terminal disclaimer.

(21) Appl. No.: 15/192,582

(22) Filed: Jun. 24, 2016

(65) Prior Publication Data

US 2017/0018410 A1    Jan. 19, 2017

Related U.S. Application Data

(63) Continuation-in-part of application No. 14/136,625, filed on Dec. 20, 2013, now Pat. No. 9,378,933.

(Continued)

(51) Int. Cl.
*H01J 37/32* (2006.01)
*A61L 2/14* (2006.01)
(Continued)

(52) U.S. Cl.
CPC .......... *H01J 37/32568* (2013.01); *A61L 2/14* (2013.01); *B01J 19/088* (2013.01);
(Continued)

(58) Field of Classification Search
None
See application file for complete search history.

(56) References Cited

U.S. PATENT DOCUMENTS

| | | |
|---|---|---|
| 4,780,277 A | 10/1988 | Tanaka et al. |
| 2007/0193448 A1 | 8/2007 | Tanaka et al. |
| 2008/0193327 A1 | 8/2008 | Vauge |

OTHER PUBLICATIONS

D. Pai et al., "Nanosecond repetitively pulsed discharges in air at atmospheric pressure—the glow regime", Plasma Sources Science and Technology, vol. 18, 2009, 8 pages.
(Continued)

*Primary Examiner* — Kishor Mayekar
(74) *Attorney, Agent, or Firm* — Berenato & White, LLC

(57) ABSTRACT

An apparatus for generating a flow of reactive gas for decontaminating a material, surface or area, comprises a first electrode member comprising a first plurality of conductive surfaces and a second electrode member comprising a second plurality of conductive surfaces. The second electrode member is arranged in spaced relationship with the first electrode member to define a reactor channel. The conductive surfaces are exposed to the reactor channel so as to form air gaps between the first plurality of conductive surfaces and the second plurality of conductive surfaces. An air blower generates a flow of air through the reactor channel. An electric pulse generator repetitively generates voltage pulses between the first and second electrode mem-
(Continued)

bers so as to produce glow discharges in the air gaps between the conductive surfaces of the first plurality and the conductive surfaces of the second plurality, the voltage pulses being generated at time intervals less than 1 millisecond and voltage pulse duration less than about 500 ns, the glow discharges being adapted to transform part of the flow of air into reactive gas. An output section delivers the reactive gas from the reactor channel to a sample or region to be decontaminated or treated.

32 Claims, 16 Drawing Sheets

Related U.S. Application Data

(60) Provisional application No. 61/918,291, filed on Dec. 19, 2013.

(51) Int. Cl.
*A61L 9/22* (2006.01)
*A61L 2/26* (2006.01)
*B01J 19/08* (2006.01)
*H05H 1/48* (2006.01)
*H05H 1/46* (2006.01)
*A61L 2/00* (2006.01)
*A61L 2/20* (2006.01)

(52) U.S. Cl.
CPC .. *H01J 37/32018* (2013.01); *H01J 37/32027* (2013.01); *H01J 37/32541* (2013.01); *H01J 37/32844* (2013.01); *H05H 1/48* (2013.01); *A61L 2/0094* (2013.01); *A61L 2/202* (2013.01); *A61L 2202/11* (2013.01); *A61L 2202/21* (2013.01); *B01D 2258/06* (2013.01); *B01D 2259/4508* (2013.01); *B01D 2259/818* (2013.01); *B01J 2219/0875* (2013.01); *B01J 2219/0898* (2013.01); *H05H 2001/4697* (2013.01); *H05H 2001/483* (2013.01); *H05H 2245/1225* (2013.01); *Y02C 20/30* (2013.01)

(56) References Cited

OTHER PUBLICATIONS

D. Pai et al., "Transitions between corona, glow, and spark regimes of nanosecond repetitively pulsed discharges in air at atmospheric pressure", Journal of Applied Physics, vol. 107, 2010, 15 pages.
F. Tholin et al., "Images of a Nanosecond Repetitively Pulsed Glow Discharge Between Two Point Electrodes in Air at 300 K and at Atmospheric Pressure", IEEE Transactions on Plasma Science, vol. 39, No. 11, Nov. 2011, pp. 2254-2255.
D. Pai et al., "The Structure of Nanosecond Repetitively Pulsed Spark Discharges in Air", IEEE Transactions on Plasma Science, vol. 39, No. 11, Nov. 2011, pp. 2258-2259.

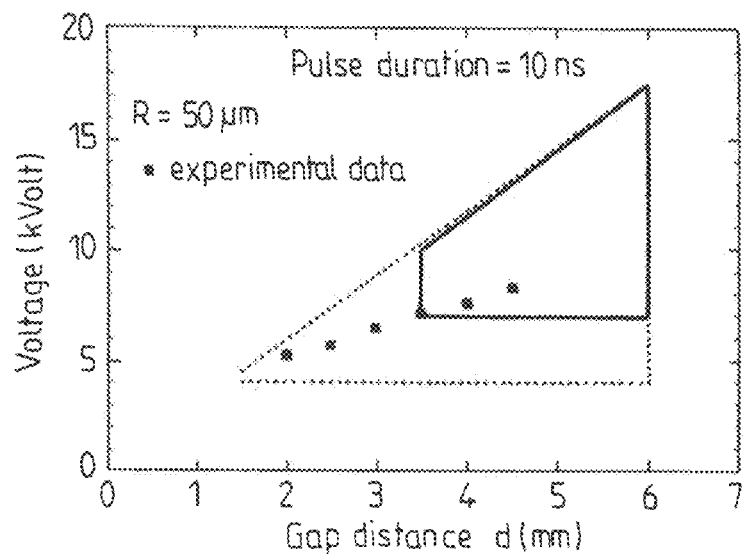
FIG.6
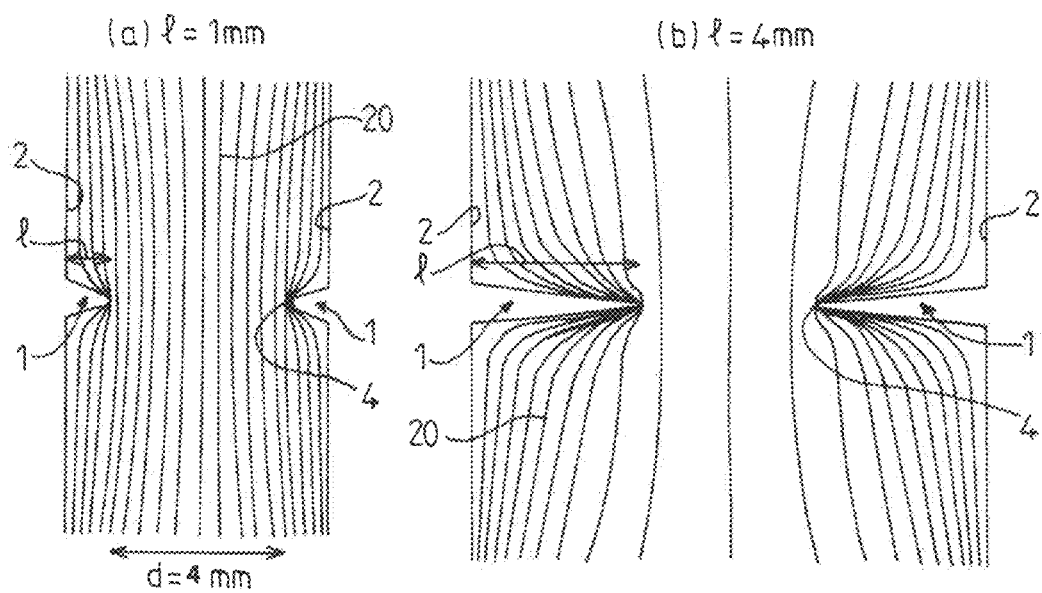
FIG.7a  FIG.7b
FIG.7

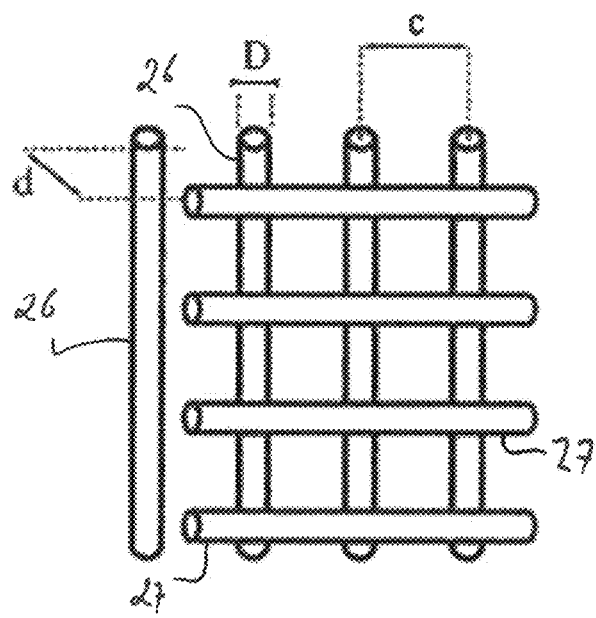
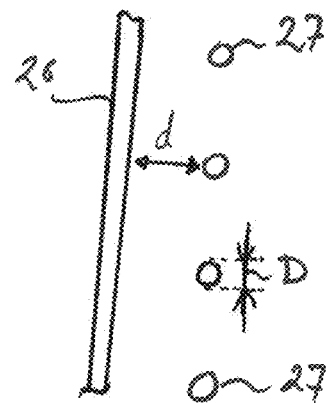
Fig. 20
Fig. 21
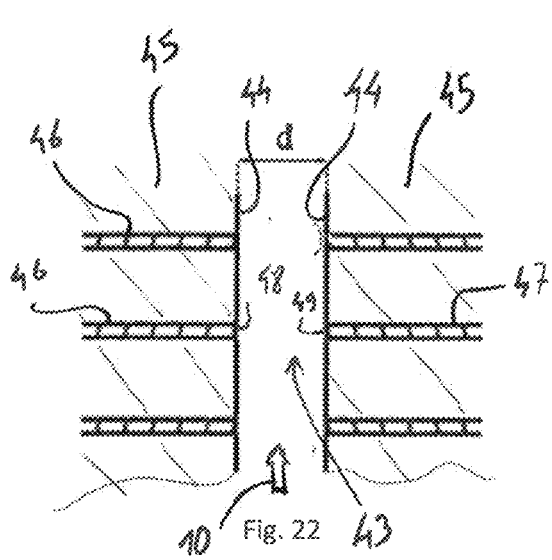
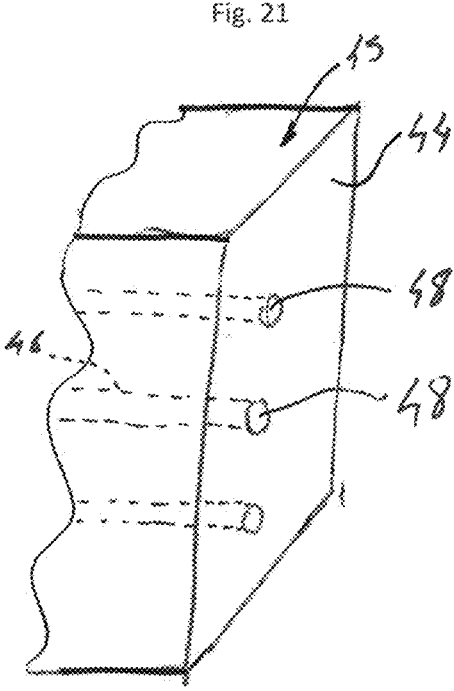
Fig. 22
Fig. 23

APPARATUS AND METHODS FOR GENERATING REACTIVE GAS WITH GLOW DISCHARGES

CROSS-REFERENCE TO RELATED APPLICATIONS

This application is a Continuation-in-Part of U.S. application Ser. No. 14/136,625, filed Dec. 20, 2013, and claims priority to U.S. Provisional Application No. 61/918,291, filed Dec. 19, 2013, the entire disclosure of which is incorporated herein by reference.

STATEMENT REGARDING FEDERALLY SPONSORED RESEARCH OR DEVELOPMENT

This invention was made with government support under contract TR001085 awarded by the National Institutes of Health. The Government has certain rights in the invention.

FIELD OF THE INVENTION

The invention relates to the technical field of plasma generation in air, in particular to apparatuses and methods for generating plasma in air with non-thermal electrical discharges to treat or decontaminate materials, surfaces, biological systems or tissues, areas, gases, and liquids.

BACKGROUND

Non-thermal air plasmas contain reactive chemical species (reactive gases) that make them suitable for applications such as surface priming, decontamination, sterilization, and biomedical treatments such as skin treatments. Reactive gas as employed herein refers to non-thermal air plasma. Decontamination as employed herein refers to the killing or suppression of biological agents such as bacteria, prions, viruses, cells, spores, biofilms and the like.

At atmospheric pressure, glow discharges in air easily transition into spark discharges that significantly heat the gas, which is problematic for applications sensitive to temperature. Therefore there remains a need to provide a non-thermal means of decontamination.

SUMMARY

Aspects of the invention aim to provide efficient methods and devices for producing non-thermal plasmas in air at or near ambient temperature, especially below 400 K. Aspects of the invention aim to obtain an efficient Nanosecond Repetitively Pulsed (NRP) glow discharge in air at atmospheric pressure and ambient temperature. Aspects of the invention aim to provide practical apparatuses, especially in a portable format suitable for surface decontamination or sterilization of surfaces, materials, biological tissues, liquids, and ambient atmospheres in buildings.

In an embodiment, the invention provides an apparatus for generating a flow of reactive gas, comprising:
 a reactor channel for receiving an incoming flow of air,
 first and second electrode members made of an electrically conductive material, each of the first and second electrode members having at least one active surface exposed to the reactor channel, wherein the at least one active surface of the first electrode member and the at least one active surface of the second electrode member are arranged in spaced relationship to define an air gap therebetween in the reactor channel, wherein the first electrode member comprises a first plurality of active surfaces turned towards the second electrode member, so that an air gap is formed between each of the first plurality of active surfaces and the at least one active surface of the second electrode member, wherein each active surface of the first electrode member has a dimension lower than 2 mm in at least one direction transverse to the air gap, and an electric pulse generator configured to repetitively generate voltage pulses between the first and second electrode members so as to produce glow discharges in the air gaps between the first plurality of active surfaces and the at least one active surface of the second electrode member, the voltage pulses being generated at time intervals less than 1 millisecond and voltage pulse duration less than about 500 ns, and preferably less than 100 ns, the glow discharges being adapted to transform part of the incoming flow of air into reactive gas at a delivery temperature, wherein a difference between the delivery temperature of the reactive gas and a temperature of the incoming flow of air is no more than 200 K, wherein the reactive gas comprises free radicals and molecules and atoms in electronic excited states, as well as positive and negative ions.

According to embodiments, such an apparatus may comprise one or more of the features below.

In an embodiment, the apparatus further comprises an air blower for generating the incoming flow of air through the reactor channel, and an output section for delivering the reactive gas from the reactor channel to a sample or region to be treated.

In an embodiment, the apparatus further comprises a hollow envelope made of an electrically insulating material, the hollow envelope having a tubular shape with a first open end connected to the air blower and a second open end connected to the output section of the apparatus, wherein the first electrode member and second electrode member are arranged on inner surfaces of the hollow envelope to define the reactor channel within the hollow envelope.

In an embodiment, the air blower has an input connected to the atmosphere for sucking ambient air and an output connected to the reactor channel for blowing the flow of air into the reactor channel.

Such small-sized active surfaces on the first and/or second electrode member may be obtained in a number of different ways. In an embodiment, the first electrode member comprises a first plurality of conductive elements extending towards the second electrode member, wherein the active surfaces of the first electrode member are provided at a tip of each conductive element turned towards the second electrode member.

Such conductive elements extending towards the second electrode member may be made in different geometries, e.g. thin plates, sharp blades such as razor blades, thin wires and sharp pins. They can also be hollow tubes with an open end exposed to the air gap, with wall thickness less than 2 mm, preferably less than about 500 μm, sharp protrusions, sawtooth-like structures such as comb-like structures, serrated blades, honeycombs, grooves, trusses or small spherical dots placed on top of electrically conductive or insulating materials. Each electrically conductive element has at least one portion, i.e. the active surface, in contact with the air gap, and this portion has a small dimension (thickness, diameter, radius of curvature, protrusion, recess) less than 2 mm, preferably less than 500 μm.

Preferably, the conductive elements of the first electrode member are spaced along at least one direction transverse to the air gaps.

In embodiments, an electrically insulating body has an inner surface that defines the reactor channel for receiving the incoming flow of air. In that case, the conductive elements of the first and/or second electrode member have a base portion embedded in the electrically insulating body and a tip portion exposed to the reactor channel.

The tip portion may be arranged in different ways with respect to the electrically insulating body, e.g. protruding from the inner surface of the electrically insulating body into the reactor channel, flush with the inner surface of the electrically insulating body or arranged at the bottom of a recess provided in the inner surface of the electrically insulating body.

In another embodiment, the first electrode and/or second member comprises thin wire, wherein a radius of said thin wire is less than 0.2 mm, preferably less than about 500 µm.

In an embodiment, the active surfaces of the first electrode member and the active surfaces of the second electrode member are arranged at corresponding positions so as to form a plurality of pairs of active surfaces each comprising a first active surface of the first electrode member and a second active surface of the second electrode member and an identical or non-identical air gap between the first and second active surfaces.

All the above-described embodiments of the first electrode member are applicable to the second electrode member. However, there is no absolute requirement that the second electrode member be made in the same way as the first electrode member. In an embodiment, the second electrode member comprises an active surface of large dimensions, e.g. planar or cylindrical with a larger radius, forming air gaps with each active surface of the first electrode member. The first electrode member and the second electrode member can be arranged in any geometrical way on both sides of the air gap, as long as their respective active surfaces are turned towards each other, e.g. in a parallel geometry or in a non-parallel, e.g. tapered, geometry.

The first and/or the second electrode member may comprise a conductive sheet arranged parallel to the reactor channel. Preferably, the conductive sheet of the second electrode member is arranged parallel or concentric to the conductive sheet of the first electrode member. However, such conductive sheets are optional. In other embodiments, the first and/or the second electrode member is made without such conductive sheet.

In an embodiment, the geometry of the electrode members and the operating parameters of the electric pulse generator may be selected so as to provide an intense and stable glow discharge between the active surfaces.

For that purpose, the following parameters may be employed:
 a width of the air gap between the active surfaces of the first and second electrode members between about 1 and 100 mm, preferably between about 2 mm and about 20 mm.
 a small dimension of the active surfaces in a direction transverse to the air gap, e.g. diameter, thickness or radius of the active surfaces smaller than about 2 mm, preferably smaller than about 500 µm.
 a pulse repetition frequency or averaged pulse repetition frequency of the electric pulse generator between about 1 kHz and about 500 kHz. The time interval between the pulses may be variable, preferably between 2 microseconds and 1 millisecond. In other words, a plurality of voltage pulses are generated in succession during the active plasma generation, where the average duration between voltage pulses is less than 1 millisecond.
 a pulse amplitude of absolute value between about 1 kV and about 50 kV, preferably between about 5 kV and about 30 kV. In embodiments; the pulse amplitude is allowed to change from pulse to pulse.
 a voltage pulse duration smaller than about 500 ns, preferably between about 0.1 ns and about 100 ns. The shorter durations in this range enable to generate more uniform glow discharges. In embodiments; the pulse duration is allowed to change from pulse to pulse. The pulse duration may be defined as the width of the pulse at 80% or 90% of the voltage amplitude.

In an embodiment, the pulse amplitude, pulse duration, or time interval between successive high voltage pulses may vary from pulse to pulse.

In an embodiment, the apparatus further comprises a length of coaxial cable connecting the electric pulse generator to an electrode member.

In an embodiment, the first electrode member is connected to the electric pulse generator and the second electrode member is connected to an electrical ground potential, i.e. in a Plus (+) vs. Ground connection configuration or Minus (−) vs. Ground connection configuration. Alternatively, the + vs. − connection configuration of the electrode members is also possible. Alternatively, the polarity of the electrodes may change from pulse to pulse, i.e. does not need to stay always positive or always negative or always at ground.

In an embodiment, an alternative (ac) or a constant (dc) voltage may be superimposed to the high voltage pulses, as a way to sustain background ionization between successive high voltage pulses in order to enhance the production of active species. Further details about the generation of such superimposed voltages can be found in "Experimental investigation of dielectric barrier discharge plasma actuators driven by repetitive high-voltage nanosecond pulses with dc or low frequency sinusoidal bias" D. F. Opaits et al. J. Appl. Phys. 104, 043304 (2008). Another relevant source of information is C. H. Kruger et al., "Non-Equilibrium Discharges in Air and Nitrogen Plasmas at Atmospheric Pressure", Pure and Applied Chemistry, Vol. 74, No. 3, pp. 337-347, March 2002.

In an embodiment the high voltage pulses are applied in burst mode, with variable periods of interruption between successive series of pulses. Likewise, the sustaining ac or dc voltage may also be applied in burst mode, independently of the high voltage pulses.

In an embodiment, the apparatus further comprises a power feed block connected to the electric pulse generator and the air blower for feeding electrical power to the electric pulse generator and the air blower.

In an embodiment, the invention provides a method for generating a flow of reactive gas, comprising:
  receiving an incoming flow of air in a reactor channel,
  providing first and second electrode members made of an electrically conductive material, each of the first and second electrode members having at least one active surface exposed to the reactor channel, wherein the at least one active surface of the first electrode member and the at least one active surface of the second electrode member are arranged in spaced relationship to define an air gap therebetween in the reactor channel, wherein the first electrode member comprises a first plurality of active surfaces turned towards the second electrode member, so that an air gap is formed between each of the first plurality of active surfaces and the at least one active surface of the second electrode member, wherein each active surface of the first electrode member has a dimension lower than 2 mm in at least one direction transverse to the air gap, and repetitively generating voltage pulses between the first and second electrode members so as to produce glow discharges in the air gaps between the first plurality of active surfaces and the at least one active surface of the second electrode member, the voltage pulses being generated at time intervals less than 1 millisecond and voltage pulse duration less than about 500 ns, and preferably less than 100 ns, the glow discharges being adapted to transform part of the incoming flow of air into reactive gas at a delivery temperature, wherein a difference between the delivery temperature of the reactive gas and a temperature of the incoming flow of air is no more than 200 K, wherein the reactive gas comprises free radicals, ions and molecules and atoms in electronic excited states.

In an embodiment, the method further comprises delivering the reactive gas from the reactor channel to a sample or region to be treated, e.g. decontaminated.

The temperature of the reactive gas should be sufficiently low for the contemplated application and targeted surface. In an embodiment, especially for biomedical applications, a temperature difference between the reactive gas delivered from the reactor channel and an ambient atmosphere is lower than about 50 K. Such temperature difference may be slightly higher for other applications, e.g. up to about 100 K or 200 K.

BRIEF DESCRIPTION OF THE DRAWINGS

These and other aspects of the invention will be apparent from and elucidated with reference to the embodiments described herein, and by way of example, with reference to the drawings.

FIG. 6 is a parametric representation of operating domains in which a stable glow discharge may be obtained for different flow parameters.

FIG. 7 is a diagrammatic representation of equipotential lines in an air gap as a function of the distance between the tip of the pin and a backing plane, i.e. pin length.

FIG. 20 is a perspective view of first and second electrode members made of parallel thin wires.

FIG. 21 is a side view of the first and second electrode members of FIG. 20.

FIG. 22 is a cross-sectional view of a reactor channel defined by the inner surface of an electrically insulating body, in a first embodiment.

FIG. 23 is a perspective view of an insulating body with embedded electrode members.

DETAILED DESCRIPTION OF THE EMBODIMENTS

Figure 1:
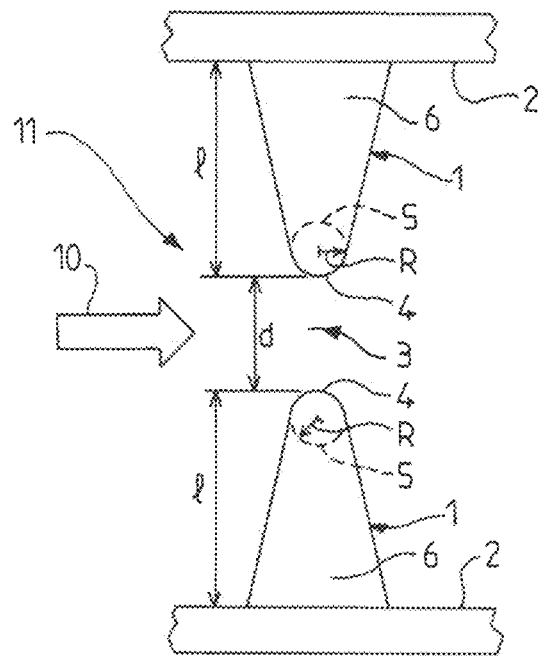
FIG. 1 is a diagrammatic representation of two electrically conductive pins that may be employed in an embodiment.

Apparatuses and methods for generating non-thermal plasmas in air according to the invention will now be described. The apparatuses and methods of the invention employ glow discharges generated between electrically conductive electrode members, at least one of which comprises structures having a small dimension in at least one direction transverse to the air gap, e.g. pins, plates, sharp blades, thin wires, sharp protrusions, sawtooth-like structures such as comb-like structures, serrated blades, honeycombs, grooves, trusses or small spherical dots. Accordingly, the properties of a glow discharge generated between a pair of electrically conductive pins will be discussed first. In the text below, "pin" or 'conductive pin' may be used instead of "electrically conducting pin" for the sake of simplicity.

The generation of Nanosecond Repetitively Pulsed (NRP) electrical current between two electrically conducting bodies separated by an air gap gives rise to three observable regimes as a function of the applied voltage.

In a first regime known as corona, a halo is observed at close proximity to one of the conducting bodies or both but not filling the gap therebetween. From a physical point of view, a conducting plasma channel, e.g., emitted streamer, does not reach the opposite body. The energy deposited is lower than 10 µJ per pulse and the resulting gas heating is negligible.

In a second regime known as glow, silent emission of light is observed throughout the air gap. From a physical point of view, a conducting plasma channel crosses the air gap from one conducting body to the other, e.g., in the form of an emitted streamer and return wave or other ignition process. The energy deposited is lower than 100 µJ per pulse and resulting gas heating is typically lower than 200 K. The conduction current intensity I between the two conducting bodies is typically less than 1 A.

In a third regime known as spark, the luminous intensity is considerably higher and an intense emission of light is accompanied by a crackling noise. A uniform discharge is obtained across the gap that causes ionization in volume without any observable streamer structure. The energy deposited is higher than 100 µJ per pulse and resulting gas heating can reach several thousand Kelvin. The conduction current intensity I between the two conducting bodies is typically more than 1 A. The transition from glow to spark regime is caused by a thermal instability that triggers a chain reaction. Accordingly, a very sharp increase in emitted light intensity is observed.

In the above description of discharge regimes, conduction current must be distinguished from capacitive current. When a high voltage pulse is applied across a pair of electrode pins in the glow regime, the typical voltage and current waveforms recorded across the electrodes have the forms shown in FIG. 18. The total current comprises two components, a capacitive current (also called displacement current) and a conduction current. The capacitive current is related to voltage via the relation:

$$I_{capacitive} = C\frac{dV}{dt}$$

where C is the capacitance of the pair of electrodes. For pin electrodes across a gap of a few millimeters, the value of C is typically in the range of about 1-100 pF (picofarad).

The conduction current is defined as the difference between the total current in the circuit connected to the electrodes when a plasma is present and the total current when the plasma is not present. It is possible to measure the current without plasma, for instance by slightly increasing the gap distance between the electrodes until the discharge extinguishes. Alternatively, if the capacitance C is known, the conduction current can be obtained from the following relation:

$$I_{conduction} = I_{total} - C\frac{dV}{dt}$$

Figure 18:
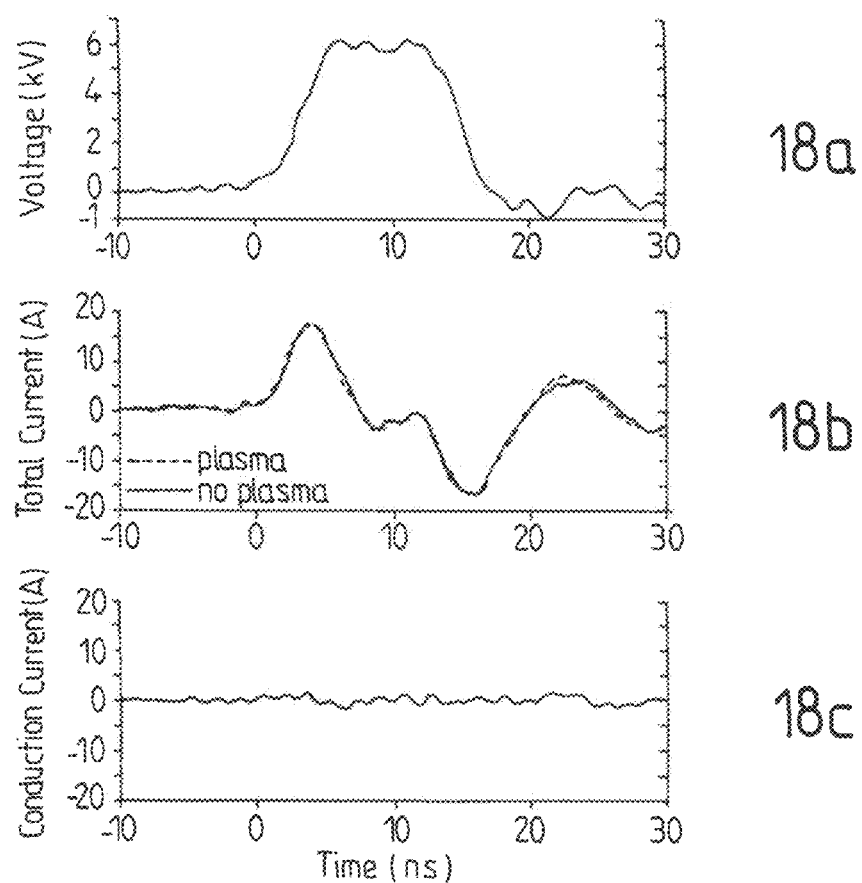
FIG. 18 is a diagram representing the applied voltage across electrodes (FIG. 18a), the measured total current flowing through the pins with and without plasma (FIG. 18b), and the conduction current obtained as the difference between the total current with plasma minus the total current without plasma (FIG. 18c).

As can be seen in FIG. 18, the conduction current remains below approximately 1 A in a glow discharge, whereas the capacitive current can reach several amperes.

The NRP glow regime is particularly interesting because it does not heat the gas significantly, much like the corona discharge, yet it produces a significant amount of active species, with much higher energy deposited than in the corona regime. Thus the glow regime is of great interest for the development of applications such as surface treatment or biomedical applications and can only be obtained with very specific conditions of electrode geometry and pulse characteristics.

FIG. 1 is a diagrammatic representation of an electrode arrangement that may be employed to produce an NRP glow discharge. Two conductive pins 1 are arranged in a tip-to-tip configuration with an air gap 3 between the pins 1. Each conductive pin 1 is backed by a conductive plane located at distance l from the pin tips, e.g. a metallic sheet 2 that is only partially shown. The gap distance between the two pins 1 is noted d. The pin 1 has a sharp tip 4 which is characterized by the radius R of an osculating circle 5. R is also referred to as the radius of curvature of the tip. The metallic sheet 2 may be planar or curved. The specific geometry of the pin body 6 is not influential on the electric phenomena discussed below. It may be cylindrical, conical, planar or other.

The electrode arrangement of FIG. 1 is connected via suitable conductors, preferably coaxial cables, to a nanosecond pulse generator, not shown, capable of providing high voltage pulses between the two conductive pins 1.

Figure 2:
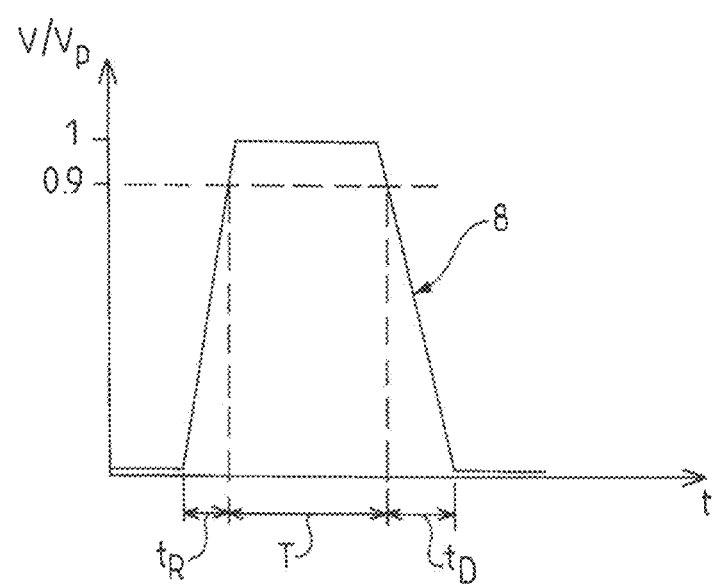
FIG. 2 is a diagrammatic representation of an electric pulse that may be employed in an embodiment.

FIG. 2 is a diagrammatic representation of a high voltage pulse 8 that is applied to one of the two conductive pins 1, while the other conductive pin 1 is connected to an electrical mass at ground potential. The amplitude of the voltage applied across the conductive planes 2 is denoted $V_p$. The high voltage pulse has a duration T defined as the width of the pulse at 90% of the voltage amplitude $V_p$. The rise time denoted by $t_R$ is preferably less than T, and the decay time denoted by $t_D$ is also preferably less than T. The pulse repetition frequency denoted by PRF is in the range between about 1 and 1000 kHz, preferably between about 5 to 500 kHz. The conduction current intensity through the pair of pins 1 is noted I.

The working gas is air, which can either be ambient air with an inherent humidity or dry air, e.g., either desiccated ambient air or air provided by a gas cylinder. An air flow 10 flows at velocity v between the conductive planes 2, substantially parallel to the conductive planes 2 as seen FIG. 1. The velocity v of the working gas or air is preferably from about 0.1 to about 100 m/s inside the reactor channel 11 defined between the conductive planes 2 as seen in FIG. 1.

Figure 3:
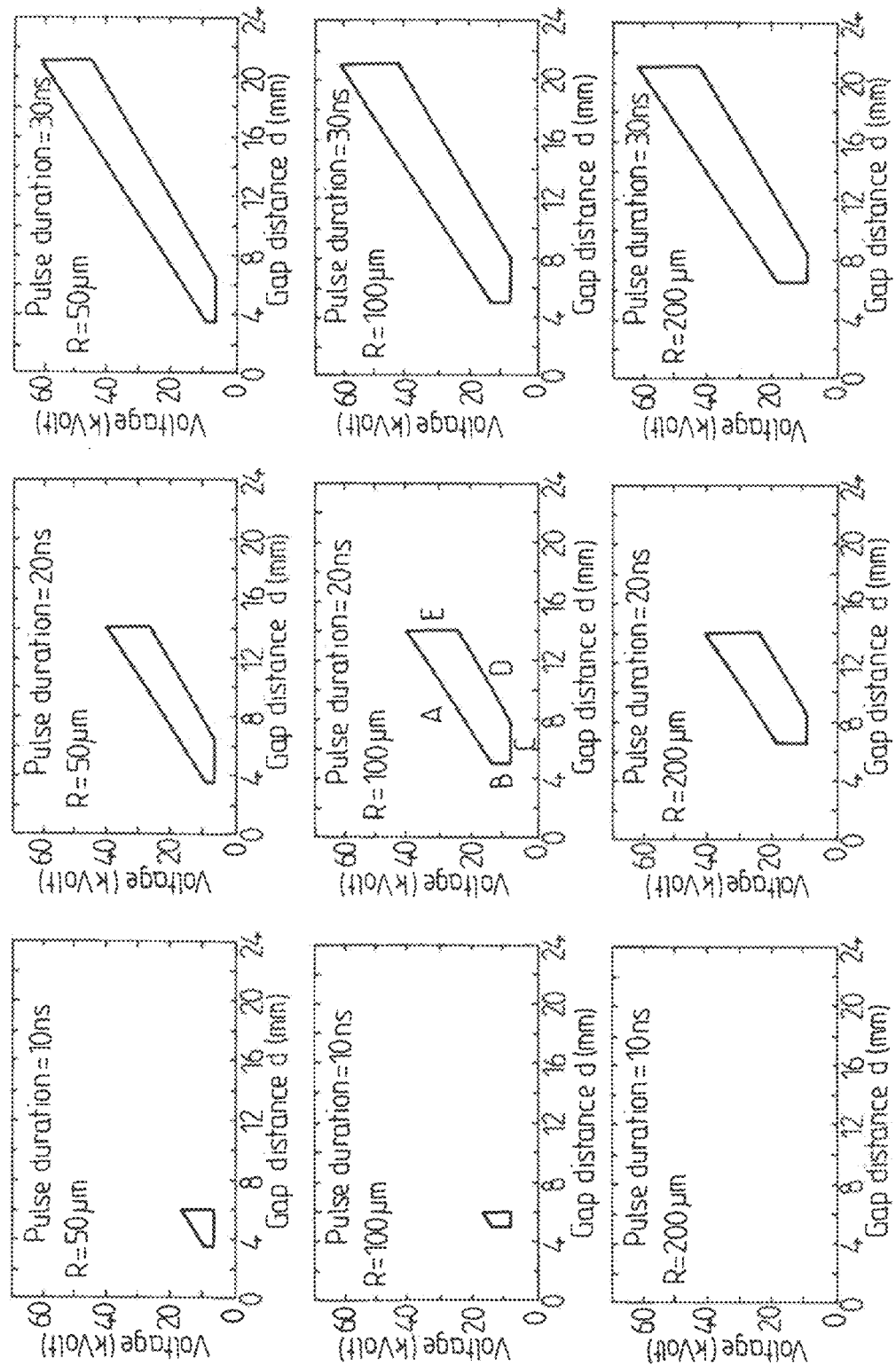
FIG. 3 is a parametric representation of operating domains in which a stable glow discharge may be obtained.

The diagrams of FIG. 3 approximately define conditions in which a glow discharge may be produced in the working gas between the pins 1. The operating domains of existence of the glow discharge are delineated by trapezoids as a function of the applied voltage $V_p$ and the gap distance d for various illustrative values of the radius of curvature R of the pin tips, i.e., 50 µm, 100 µm and 200 µm, and various illustrative values of the pulse duration T, i.e. 10 ns, 20 ns and 30 ns. The domains shown in FIG. 3 are for a fixed PRF of 30 kHz. The working gas is ambient air. These results were obtained with an air flow parallel to the longitudinal direction of the pins 1 and without any conductive plane backing. The gas velocity is 1.5 m/s.

In the central diagram of FIG. 3, the domain of existence of the glow discharge is delineated by a trapezoid with boundaries A, B, C, D and E. The physical meaning of those frontiers is further explained below. The discussion applies to the other diagrams of FIG. 3 as well.

Boundary A: this boundary is limited by the voltage at which the glow to spark transition occurs. It can be determined from the following equation: $V=E_{breakdown} d+V_{CF}$ where $E_{breakdown}=30$ kV/cm is the approximate breakdown voltage in ambient air, d is the gap distance, and $V_{CF}$ is the cathode fall voltage of nanosecond repetitively pulsed discharges, which has been determined to be around 2 kV. Above this boundary, the discharge becomes a spark.

Boundary B: this boundary corresponds to a minimum gap distance $d_{min}$ below which a glow discharge cannot be established in air. The values were determined experimentally as will be explained with reference to FIG. 4 herein below.

Boundary C: This boundary corresponds to a minimum value of the pulse voltage $V_p$, denoted $V_{min}$, below which a glow discharge cannot be established in air. The values were determined experimentally as will be explained with reference to FIG. 5 herein below.

Boundary D: This boundary corresponds to the transition between the corona and glow discharge regimes in air. It is approximately defined as the operating conditions where the luminous emission caused by the discharge visually fills up the entire gap between the electrodes. The slope is approximately 27 kV/cm. Below this boundary, the discharge will simply exist as a corona.

Boundary E: This boundary is determined by the duration T of the high voltage pulse. This maximum gap distance may be approximately determined as 0.7 mm per nanosecond of pulse duration.

The operating domains of existence of the glow discharge become broader with pulse duration, but at the expense of an increased voltage $V_p$.

The use of sharp pins 1 with small radius of curvature R reduces the minimum gap distance $d_{min}$ and required operating voltage $V_p$. The use of sharp pins makes it possible to use shorter pulse durations. For example, with a pulse of 10 ns duration, the glow discharge may only be obtained with a radius of curvature R less than 200 microns, as shown in FIG. 3.

Figure 4:
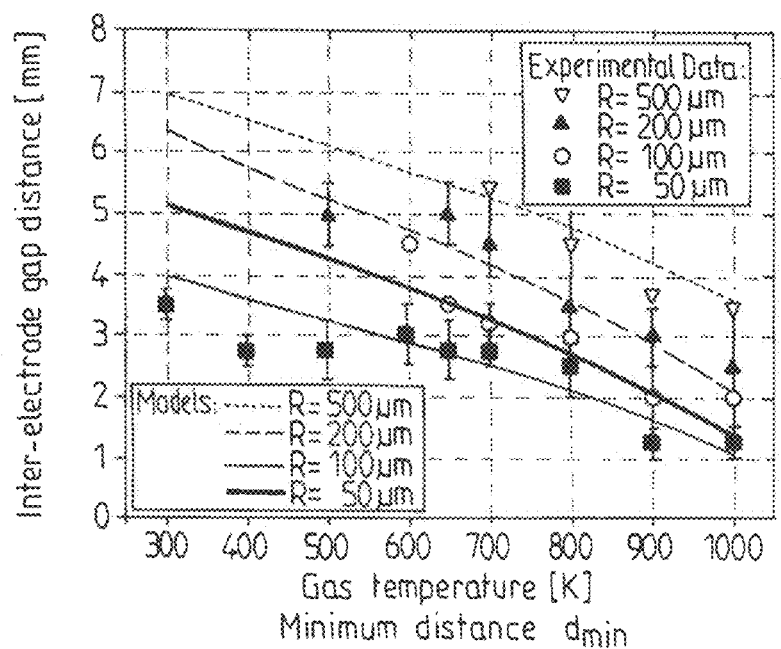
FIG. 4 is a diagram representing a minimum inter-electrode gap distance for which a glow discharge regime may be obtained, as a function of gas temperature and pin sharpness.

FIG. 4 illustrates the evolution of the minimum interelectrode gap distance $d_{min}$, i.e., boundary B, as a function of radius of curvature R and working gas temperature in Kelvin. Experimentally observed data points are shown with a margin of uncertainty limited by vertical lines terminated by horizontal hyphens. Theoretical predictions are shown by overlaid lines for comparison. The results shown in FIG. 4 are for a fixed PRF of 30 kHz and fixed gas velocity of 1.5 m/s. The working gas is ambient air. As can be seen in FIG. 4, that the $d_{min}$ increases with increasing R and reaches an approximately constant value of about 8 mm for radii of curvature greater than 200 microns. Note that these results are obtained with an air flow parallel to the longitudinal direction of the pins 1 and without any conductive plane backing.

Figure 5:
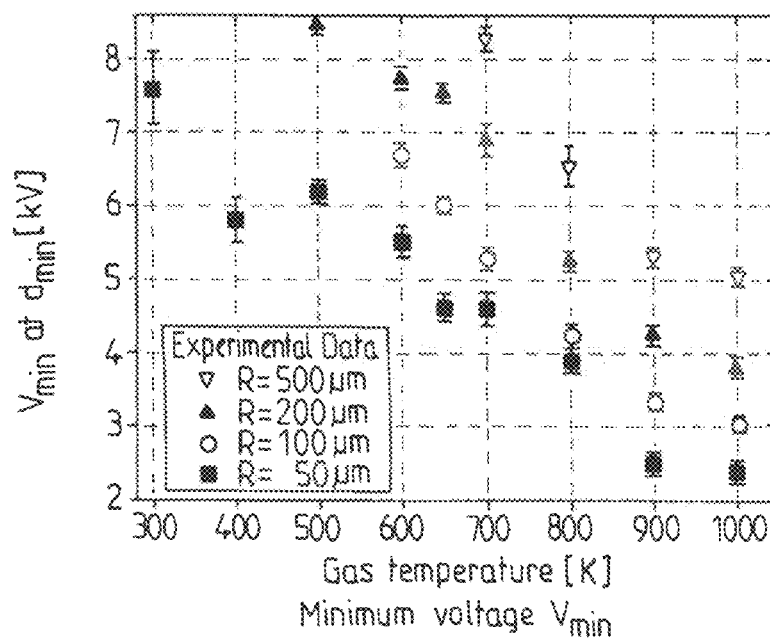
FIG. 5 is a diagram representing a minimum pulse amplitude for which a glow discharge regime may be obtained, as a function of gas temperature and pin sharpness.

FIG. 5 illustrates the evolution of the minimum voltage amplitude $V_{min}$, i.e. frontier C, as a function of radius of curvature R and working gas temperature in Kelvin. Experimentally observed data points are shown with a margin of uncertainty limited by horizontal hyphens. The results shown in FIG. 5 are for a fixed PRF of 30 kHz and fixed gas velocity of 1.5 m/s. The working gas is ambient air. The results were obtained with an air flow parallel to the longitudinal direction of the pins 1 and without any conductive plane backing.

The Influence of the Air Flow Direction and Velocity on the Operating Conditions of the Glow Discharge:

Whereas the results presented in FIGS. 3 to 5 are for a flow of gas parallel to the pins, the electrode arrangement of FIG. 1 is for a flow transverse to the conductive pins 1, i.e. perpendicular or at least not parallel to the axis (longitudinal direction) of the conductive pins 1. It was observed that the use of a transverse flow modifies the distance $d_{min}$ by a few millimeters and the voltage $V_{min}$ by a few kV because of the shorter residence time of the air molecules in the region where the discharge operates. It was observed that the typical glow discharge diameter is about 10% of the gap length. Therefore, the residence time of the gas in the discharge region is about 10 times shorter in a transverse flow than in a parallel flow.

FIG. 6 illustrates operating domains of existence of the glow discharge as a function of the gap distance d and the pulse amplitude $V_p$ and compares the domain obtained with a flow of air parallel to the axis of the pins (at PRF=30 kHz and v=1.5 m/s) with the domain obtained with a transverse flow (at PRF=10 kHz and v=0.5 m/s). It is observed that the transverse flow reduces the minimum gap distance by a few millimeters and lowers the minimum operating voltage $V_{min}$ by a few kilovolts. The different values of the frequency and velocity parameters PRF and v between the two cases have negligible effect compared to the change from a parallel to an axial flow. In conclusion, the transverse flow has the effect of enabling the glow discharge to occur over a wider operating domain, especially with smaller air gaps d.

The Influence of the PRF and Flow Velocity on the Operating Conditions of the Glow Discharge:

In general, increasing the flow velocity increases the minimum gap distance $d_{min}$ and the minimum required voltage $V_{min}$. Thus boundary B move to the right and boundaries C and D are move upwards. The minimum required voltage $V_{min}$ increases with increasing flow velocity because the amount of residual gas species, in particular electrons and charged ions left by the previous discharge at the time when the next discharge occurs is decreasing with increasing flow velocity. Therefore, it is necessary to increase the applied voltage $V_{min}$ in order to maintain the glow.

Furthermore, the minimum required voltage $V_{min}$ decreases with increasing PRF because there are more residual gas species, in particular electrons and charged ions when the next pulse occurs. Therefore maintaining the glow discharge requires a lower applied voltage as PRF increases. It was observed that the minimum voltage required to maintain a glow decreases by several kilovolts, e.g., about 2.5 kV, when the PRF increases from about 1 to 30 kHz.

It was observed that varying the PRF or velocity parameter while maintaining the ratio v/PRF (flow velocity v divided by PRF) leads to a stable minimum required voltage $V_{min}$. A practical implication is that the PRF may be set proportionally to the gas flow rate. For instance, if the flow velocity is increased from 0.5 m/s to 10 m/s in the transverse flow case illustrated in FIG. 6, it is necessary to increase the PRF by 20 times to maintain a similar domain of existence as the dotted domain in FIG. 6. In that particular case, this means a PRF of about 200 kHz.

The Influence of the Distance l Between the Electrically Conductive Surface 2 and the Tip 4 of the Pins 1 on the Operating Conditions of the Glow Discharge:

FIG. 7 illustrates the configuration of electric equipotential lines 20 between the conductive surfaces 2 for two values of the distance l (other parameters unchanged).

In FIG. 7a: l=1 mm.

In FIG. 7b: l=4 mm.

It is seen that decreasing the distance l between the pin tips 4 and the conductive planes 2 behind them changes the form of the equipotential lines, making them more parallel to the conductive plane 2 near the tip 4 of the pins 1. Therefore, the flux lines of the electric field orthogonal to the equipotential lines, along which the electric current generally flows, become more axial. This effect tends to reduce branching of the discharge and concentrate more energy per unit volume, which is beneficial for increasing the glow efficiency, i.e., the production of active chemical species. It is concluded that reducing the distance L between the pin tips 4 and the conductive plane 2 behind them causes the glow discharge to be more concentrated in space and therefore increases the productivity of active species in air for a given amount of energy transferred.

Figure 8:
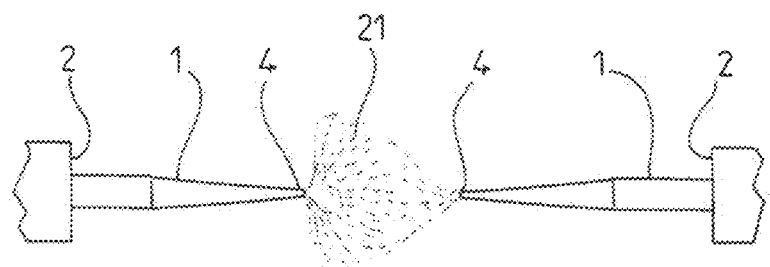
FIG. 8 is a diagrammatic representation of a glow discharge generated in an air gap between two pins without an electrically conductive backing plane.
Figure 9:
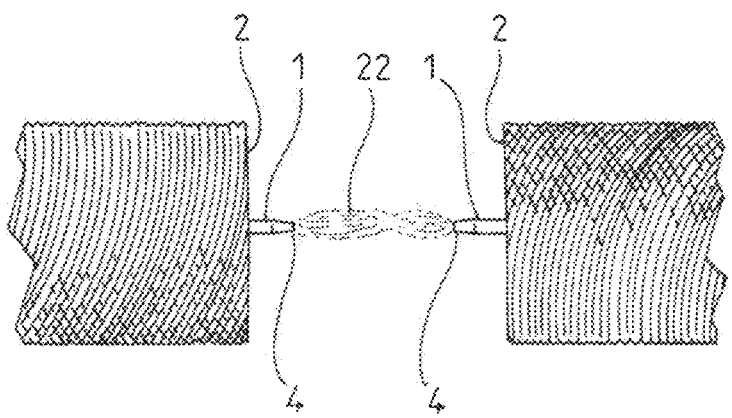
FIG. 9 is a diagrammatic representation of a glow discharge generated in an air gap between two pins with an electrically conductive backing plane.

This effect is further demonstrated in the experiments illustrated in FIGS. 8 and 9. FIGS. 8 and 9 are side-views of glow discharges 21 and 22 generated in an air gap d between two aligned, equally spaced conductive pins 1. The radius of curvature R of the pin tip 4 is 10 μm. The gap distance d is about 5 mm, the PRF is 10 kHz, and the flow is transverse to the axis of the pins 1 at a velocity of about 1 m/s.

In FIG. 8, the distance l is sufficiently large so that the conductive plane 2 has negligible effect, i.e., it may be considered absent. The glow discharge 21 is a spatially extended discharge also known as NRP Multi-Channel Glow.

By contrast, the distance is l=1 mm in FIG. 9. The glow discharge 22 now has an axial shape also known as Single Channel Glow. As a consequence, the electric energy of the glow discharge 22 is concentrated in a smaller volume than the glow discharge 21, which beneficially increases the productivity of active chemical gas species.

The active chemical gas species that may be produced by a glow discharge in air include electrons, ions, free radicals and excited molecules and atoms. More precisely, gas molecules that constitute air are excited by the glow discharges and become ionized, so that free electrons contribute to excite more atoms and molecules to generate free radicals such as atomic oxygen, atomic nitrogen, nitrogen oxides ozone, as well as OH, $H_2O_1$, HOO radicals (in presence of water vapor like in humid air), ions such as $N_2^+$, $O_2^+$, $N^+$, $O^+$, $O_4^+$, $N_4^+$, $N_2O^+$, $O_2N_2^+$, $NO^+$, $O^-$, $O_2^-$, $O_3^-$, $NO_2^-$, $NO_3^-$, or even water ion clusters (in presence of water vapor), and molecules and atoms in various vibrational and electronic excited states.

Turning now to FIGS. 10 to 15, there will now be described embodiments of a reactive, especially decontaminating gas generation apparatus that employs a plurality of pin pairs to produce a glow discharge in a reactor channel. Accordingly, the above discussion of the operating regime of glow discharges fully applies to the embodiments of the apparatus that are described herein below.

Figure 10:
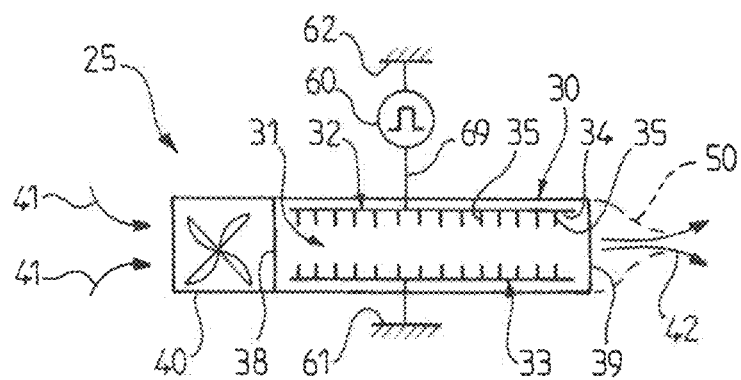
FIG. 10 is a diagrammatic functional representation of a reactive gas generation apparatus in accordance with a first embodiment.

With reference to FIG. 10, an apparatus 25 for generating a flow of decontaminating gas comprises a reactor 30 having a reactor channel 31 defined between a pair of electrode members 32 and 33 that each comprise a conducting sheet 34 and a plurality of identical pins 35 that protrude orthogonally or obliquely from the conducting sheet 34. The conducting sheets 34 of both electrode members 32 and 33 are parallel and spaced to define the reactor channel 31 between them. The pins 35 are arranged within the reactor channel 31, preferably in a one-to-one relationship to define a plurality of pin pairs having an identical or similar structure in terms of gap distance and flow orientation. Such identical structure makes it easier to establish and control a stable NRP glow discharge through the plurality of pin pairs.

The electrode members 32 and 33 may be made out of any conductive material, e.g., metal such as steel or tungsten, conductive ceramic or a semiconductor. Metals with a lower melting point than steel and tungsten can also be considered depending on the operating conditions of the apparatus. The shape, size and number of pins of the electrode members 32 and 33 may be varied depending on the total power and expected flow rate of the apparatus.

Figure 11:
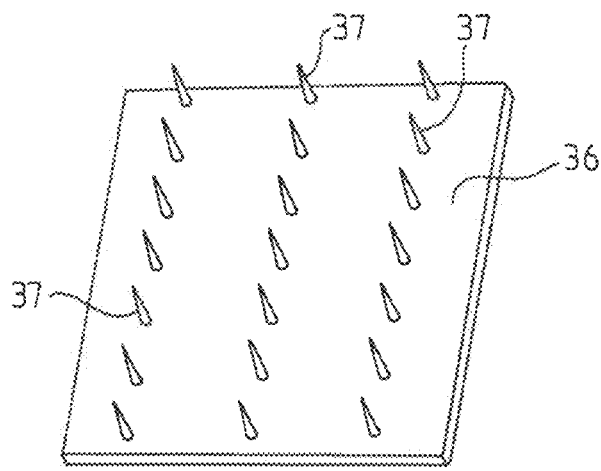
FIG. 11 is a diagrammatic perspective view of a multi-pin electrode which may be employed in the apparatus of FIG. 10.

FIG. 11 illustrates an embodiment of the electrode member comprising a rectangular sheet of conducting material 36 and a plurality of pins 37 which are distributed on a plane surface of the conductive sheet 36, as an array with a uniform pitch. Such an array with a large number of pins can be manufactured with 3D metal printers or chemical etching processes for instance. The pins 37 may be arranged in different manners on the conductive sheet 36. In a non-illustrated modification, a line of pins is employed instead of an array of pins. In a non-illustrated modification, the pins are elongated like razor blades, with a tip in the form of sharp conductive line. As discussed above, the smallest radius R of curvature at the pin tip is the most influential parameter for controlling the discharge regime, whereas other geometrical parameters of the pins may be modified in view of further considerations, such as bulk, material cost and ease of implementation.

An air blower 40 is arranged at one end of the reactor channel 31 for blowing a flow of air through the reactor channel 31 as seen in FIG. 10. The air blower 40 may draw air from the surrounding atmosphere as shown by arrows 41. In a non-illustrated modification, the air blower 40 may draw air from a controlled atmosphere, e.g., with controlled humidity, and/or through an air processing device intended to modify the humidity rate or air temperature, e.g. heater, air dryer or humidifier. The flow of air blown by the air blower 40 enters the reactor 30 through an input 38, crosses the reactor channel 31 transversely to the pins 35 and exits the reactor channel 31 through an output 39 in a modified chemical state due to the NRP glow discharge produced within the reactor channel 31, as illustrated by arrows 42.

In a non-illustrated modification, the apparatus may be provided with a bottle of additive gas configured to mix small quantities of additive gas into the flow of air upstream of the reactor channel in order to increase the reactivity of air. The additive gas may be helium. The additive gas makes less than 5% in volume of the mix and does not change the operating domain of the glow regime.

As seen in FIG. 10, an electric pulse generator 60 is configured to generate periodical short voltage pulses between the electrode members 32 and 33. The operating parameters of the pulse generator 60, in particular Pulse Repetition Frequency PRF, pulse duration T and pulse amplitude $V_p$, and the geometrical parameters of the electrode members 32 and 33, in particular radius of curvature R on the pins 35, gap distance d and pin length l are selected so as to obtain a stable glow discharge between each pair of pins. Suitable pulse generators are available from the company FID GmbH (Germany). The pulse generator may either generate a controlled voltage waveform or a controlled current waveform. In both cases a short nanosecond electric pulse is obtained.

The glow operating regime may be selected as close as possible to boundary A in order to optimize the productivity of active gas species. However, the production of heat close to boundary A may be excessive. In a preferred embodiment, the glow operating regime is selected so that the air flow temperature is increased by less than 50 K.

In selecting the glow operating regime, the voltage amplitude $V_p$ should be carefully selected. It may not be desirable for the voltage amplitude $V_p$ be too high because of the increased importance of electromagnetic interferences, increased insulation requirements, in particular for the cables connecting the pulse generator to the electrode members, and increased insulation requirements of the apparatus as a whole. Therefore, the preferred range of operation for the voltage amplitude is $V_p$ less than about 30 kV.

For a given gap distance d, X-rays may be emitted if the voltage exceeds the upper limit of the domain by several hundred percent or more.

A nozzle piece 50, as seen in FIG. 10, may be arranged at the output 39 of reactor 30 to shape and/or direct the flow of reactive gas 42 in a desired manner, e.g. convergent or divergent, straight or bent. This nozzle piece 50 may also serve the role of accelerating the flow of reactive gas 42 to the area to be treated, which is beneficial if the lifetime of the active gas species is short.

In an embodiment, the apparatus 25 is dimensioned as a portable electric appliance similar in size to an air blower, which can be used to direct a flow of non-thermal reactive gas towards any surface that requires sterilization, decontamination or disinfection, e.g., in a biomedical environment, or surface priming. In such portable appliances, electrical insulation may be provided by an external shield, e.g. in plastic material, to protect the user.

Figure 12:
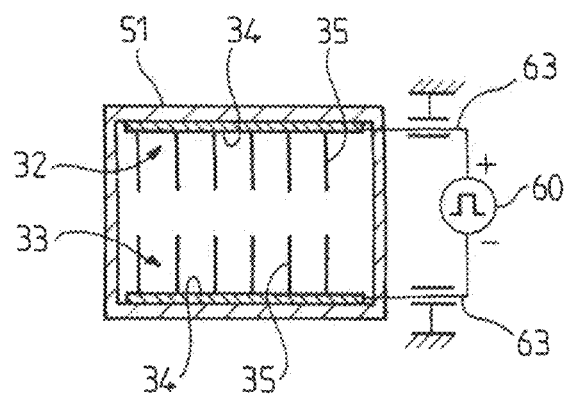
FIG. 12 is a diagrammatic sectional view of a reactor channel in an embodiment.

FIG. 12 illustrates an embodiment of the reactor 30 that comprises a tubular outer envelope 51 which is shown in cross-hatching. The outer envelope 51 is preferably made of an insulating material, e.g., plastic, and may have any cross-sectional shape, e.g., rectangular as shown, circular or other. Elements identical or similar to those of FIG. 10 are designated by the same numerals. The electrode member 32 and 33 are fixed on an inner surface of opposite walls of the outer envelope 51.

FIGS. 10 and 12 show two alternative ways of connecting the electrode members 32 and 33 to the pulse generator 60. In FIG. 12, the electrode members 32 and 33 are respectively connected to a positive and a negative terminal of the pulse generator 60, which applies a push-pull drive voltage to the electrode members 32 and 33. In FIG. 10, electrode member 33 is connected to a ground potential 61 whereas only electrode member 32 is connected to the pulse generator 60, which generates the NRP voltage signal against a ground potential 62. As shown on FIG. 12, coaxial cable 63 is preferably employed to connect the electrode members 32 and 33.

It will be appreciated that the conductive sheet 34 of an electrode member has the effect of putting all conductive pins 35 carried by the sheet 34 to the same electrical potential, in a parallel electrical connection. In other words, all the pin pairs formed by the electrode members 32 and 33 are fed in parallel by the pulse generator 60. This feature can advantageously optimize the energy efficiency of the system, as explained further below.

The pulse generator 60 has an internal impedance $R_g$ and is connected to the electrode members 32 and/or 33 via a transmission line 69 as seen in FIG. 10, or preferably via a coaxial cable 63 as seen in FIG. 12, which have an impedance $R_{line}$ preferably close to $R_g$.

In order to obtain the best energy efficiency from the apparatus 25, impedance matching should be achieved, i.e., the combined impedance of all pin pairs 35 connected to the pulse generator 60 should match the impedance of the generator $R_g$ and of the connecting line $R_{line}$. This requirement makes it possible to determine an optimal number of pin pairs.

Quantitative Example

We consider the case where the resistance of a single glow discharge is $R_{1-glow}$=100 k$\Omega$, which is typical with an applied voltage of 10 kV and a conduction current through a pin of 0.1 A, and where the pulse generator 60 and connecting line 69 have equal impedances $R_g=R_{line}$=100$\Omega$. Then the number of pins N for optimum energy efficiency, i.e., impedance matching is given by the relation:

$$N_{opt}=R_{1-glow}/R_g=1000$$

Thus the electrode member would ideally have 1000 pins under these assumptions. According to transmission line theory, the efficiency is higher than 90% if at least $N_{opt}/2$=500 pins are used. The efficiency is still higher than 30% if at least $N_{opt}/10$=100 pins are used. Thus, acceptable power efficiency can also be obtained for a number of pins much lower than the optimum number $N_{opt}$, which provides a lot of flexibility in the design of the apparatus. Similar logic applies for a number of pins greater than the optimum number.

When $N_{opt}$=1000 pins are employed, the circuit dimensioning is as follows: the total current through the reactor 30 during each voltage pulse is 100 A. The peak power delivered by the generator 60 during each pulse is 100 A×10 kV=1 MW. If the pulse duration is 10 ns and the PRF is 10 kHz, then the average power of the pulse generator 60 will be 1 MW×10 ns×10 kHz=100 Watt, which is comparable to the power of a typical light bulb.

The total number of pins serviced by a single pulse generator can be increased beyond the ideal number while maintaining optimal efficiency by engineering the transmission line. For example, a 50-$\Omega$ cable connecting the pulse generator to the pin array would ideally supply 500 pins, according to the example given above. However, if the 50-$\Omega$ cable is connected instead to two 100-$\Omega$ cables in parallel, then a total of 2000 pins could be used, i.e., 1000 at the end of each 100-$\Omega$ cable, without any theoretical power loss due to improper matching.

Figure 13:
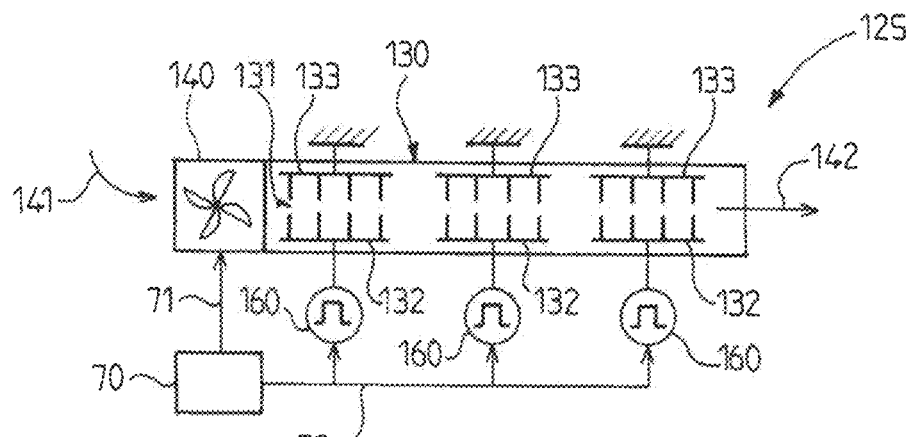
FIG. 13 is a diagrammatic functional representation of a reactive gas generation apparatus in accordance with a second embodiment.

With reference to FIG. 13, a second embodiment of the reactive gas generation apparatus will be described. Elements identical or similar to those of FIG. 10 are designated by the same numeral augmented by 100. In the apparatus 125 of FIG. 13, the reactor 130 comprises a plurality of pairs of the electrode members 132 and 133, i.e., three pairs arranged in succession in the direction of the air flow.

In addition, FIG. 13 shows a plurality of pulse generators 160, i.e., one per pair of the electrode members 132 and 133. In a non-illustrated embodiment, a single pulse generator may be employed to feed several pairs of electrodes in parallel.

FIG. 13 also shows a power feed block 70 that is employed to feed electrical power to all electrical components of the apparatus 125, namely the air blower 140 through connection 71 and the pulse generators 160 through connection 72.

Figure 16:
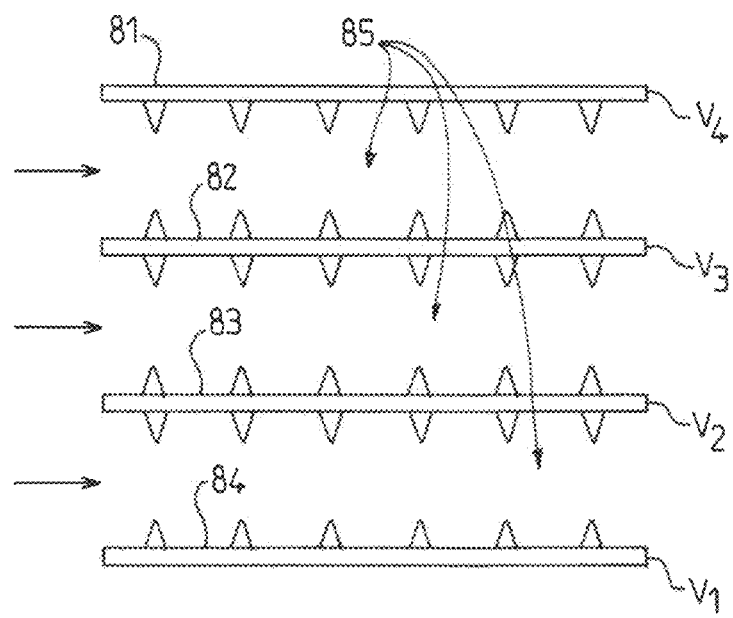
FIG. 16 is a diagrammatic functional representation of a reactive gas generation apparatus in accordance with a third embodiment.

It will be appreciated that any number of electrode members may be arranged in a reactive gas generation apparatus in accordance with the invention, depending on the expected power and total flow rate of the apparatus. FIG. 13 illustrates an embodiment with electrodes members arranged along a single reactor channel 131. In other embodiments, a plurality of similar reactor channels may be provided in parallel as in a multilayered or sandwich structure. A corresponding embodiment is illustrated on FIG. 16, where four electrode members 81, 82, 83 and 84 are arranged parallel to one another and spaced by similar distances to define three parallel reactor channels 85. Voltages V1 to V4 are applied to the electrode members 81, 82, 83 and 84 to generate a glow discharge through each reactor channel 85. In order to alternate high and low voltages, the voltages V1 to V4 may be configured so that: $V_1<V_2>V_3<V_4$ or $V_1>V_2<V_3>_4$.

In another embodiment, not shown, the parallel channels each have their own pair of electrodes. In this case, the channels must be separated by an electrically insulating material.

Figure 14:
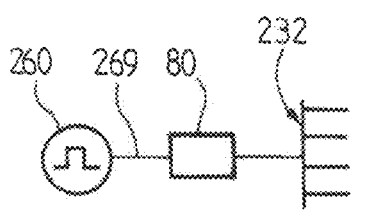
FIG. 14 is a diagrammatic representation of a pulse generator with a current limiting resistor which may be employed in an embodiment.

FIG. 14 illustrates an embodiment in which a current-limiting resistor 80 is arranged on the transmission line 269 between the pulse generator 260 and the electrode member 232. Elements identical or similar to those of FIG. 10 are designated by the same numeral augmented by 200. The current-limiting resistor 80 helps prevent accidental transition to the spark regime by creating a voltage fall proportional to current.

Figure 15:
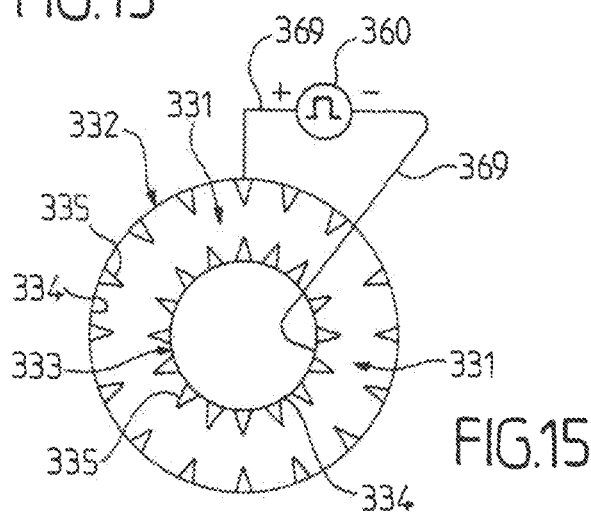
FIG. 15 is a diagrammatic sectional view of a reactor channel in another embodiment.

The electrode members may be made in different shapes. FIG. 15 illustrates an embodiment in which the electrode members 332 and 333 are made of coaxial conductive cylinders defining a reactor channel 331 having an annular shape. Elements identical or similar to those of FIG. 10 are designated by the same numeral augmented by 300.

Figure 17:
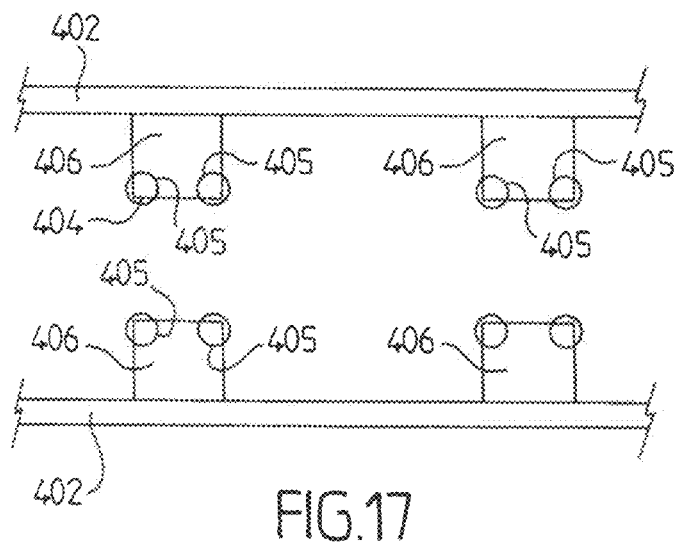
FIG. 17 is a diagrammatic representation of electrode members in another embodiment.

As indicated, the most influential geometric feature of the conductive pins is the sharp protruding edge, i.e., small radius of curvature at the tip R as discussed above. Such sharp edges may be provided on conductive pins having various shapes, e.g., cylindrical, conical, planar or other. FIG. 17 illustrates an embodiment in which the pin body 406 is an elongated blade with sharp edges 404 on osculating circles 405 at both ends of the pin body 406. Elements identical or similar to those of FIG. 1 are designated by the same numeral augmented by 400.

Figure 19:
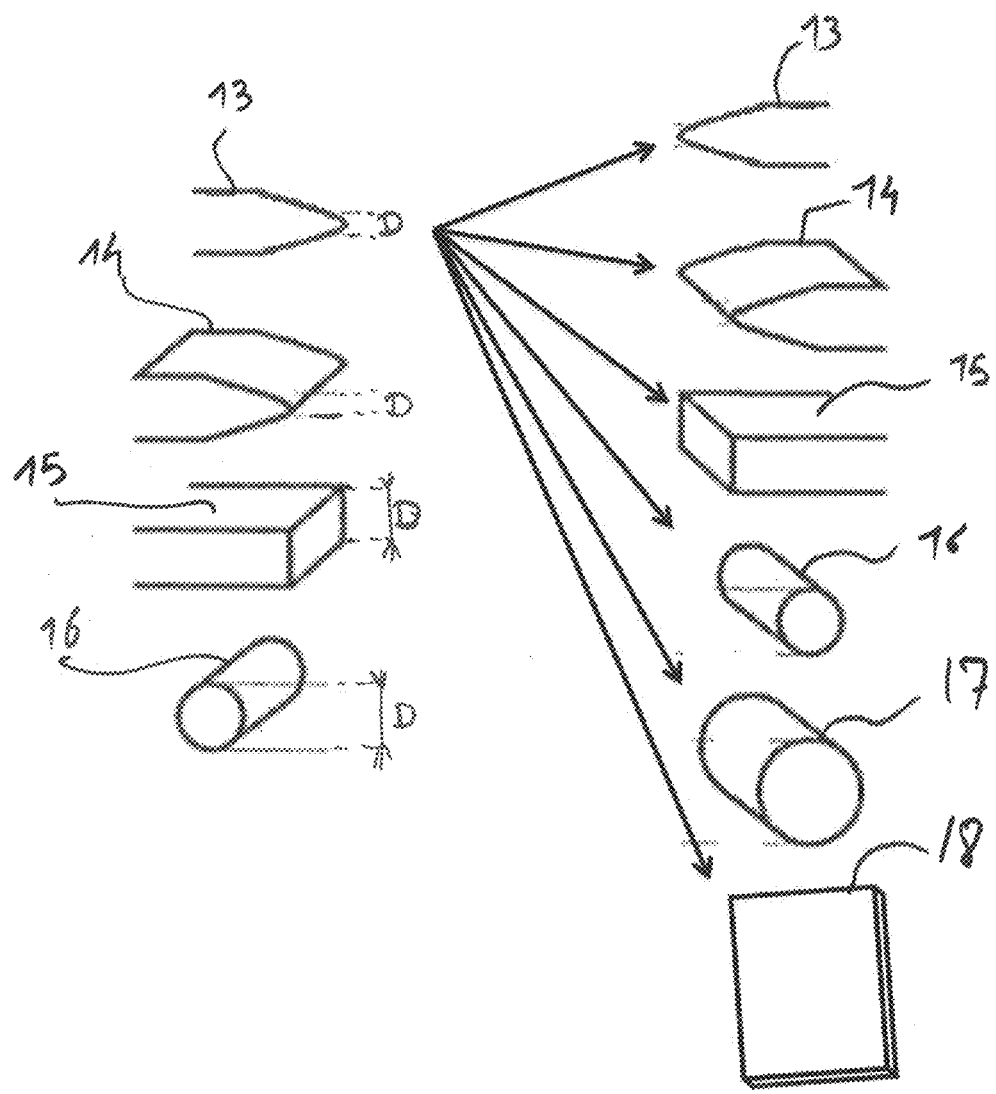
FIG. 19 is a diagrammatic representation of first and second electrode members selected among different geometries suitable for generating NRP glow discharges.

Various geometries suitable for electrode members to produce non-thermal plasma in air are shown on FIG. 19. In FIG. 19, the left-hand side column diagrammatically illustrates four geometries suitable for a first electrode member and the right-hand side column diagrammatically illustrates six geometries suitable for a second electrode member. The arrows symbolically show that any geometry shown in the left-hand side column may be combined with any geometry shown in the right-hand side column. In other words, symmetrical arrangements as well as dissymmetrical arrangements are contemplated in this diagram.

In FIG. 19, numeral 13 denotes a sharp pin with a small radius of curvature at the tip, i.e. a three-dimensional structure. Numerals 14-16 other denote two- or three-dimensional structures, namely sharp blade 14, thin plate 15 and thin wire 16. All the structures on the left-hand side have a small dimension D in at least one direction transverse to the air gap, namely diameter of osculating circle D at the tip of sharp pin 13 or sharp blade 14, thickness D of thin plate 15 and diameter D of thin wire 16.

The second electrode member may or may not have such small dimension D in at least one direction transverse to the air gap. Namely, numeral 17 denotes a large cylinder and numeral 18 denotes large planar surface.

As indicated, a conductive plane is not required to obtain NRP glow discharges in air, especially since NRP Multi-Channel Glow is also a suitable phenomenon for producing active species. Several embodiments of the electrode members that do not employ a backing conductive plane will now be described.

FIGS. 20 and 21 illustrate a pair of electrode members that may be employed in a reactor channel to produce NRP glow discharges in air. The first electrode member 26 is made of a first series of thin, parallel wires having diameter D and arranged in a first plane, whereas the second electrode member 27 is made of a second series of thin wires having diameter D and arranged in a second plane at a distance d from the first electrode member 26. The thin wires 26 and thin wires 27 may have parallel or non-parallel directions. In the example shown, they have mutually orthogonal directions, such that air gaps are obtained at each intersection between a wire 26 and a wire 27, as seen in a projection perpendicular to the first and second planes. By connecting the electrode members 27 and 26 to the electrical pulse generators as described above, stable glow discharges may be obtained in each air gap.

Thin wire can be employed in different ways to make one or both electrode members. An electrode member may be made of a wire or a group of wires having a straight or wavy or wrinkly shape. The wire or a group of wires may be arranged in a plane or bent in two-dimensional or three-dimensional shapes.

Further embodiments of a reactor that can be employed in an apparatus for generating a flow of decontaminating gas will now be described with reference to FIGS. 22 to 30. In those embodiments, the reactor channel is delimited by one or more insulating bodies, with the electrode members embedded in or arranged between the one or more insulating bodies. As insulating bodies, a number of different dielectric materials can be used such a plastic, PVC, glass, alumina, zirconia, etc.

Such insulating bodies may serve several purposes. With respect to the flow of air, the insulating bodies may be employed to define the limits of the reactor channel and therefore to configure the flow of air accordingly. With respect to the electrode members, the insulating bodies may be employed as mechanical supports and/or spacer pieces to define the positions of the electrode members in a precise and stable manner.

Turning to FIG. 22, a reactor channel 43 for receiving the flow of air 10 is shown in cross section. The reactor channel 43 is formed between the inner surfaces 44 of two insulating bodies 45. Conductive elements 46 embedded in the left-hand side insulating body 45 form the first electrode member and conductive elements 47 embedded in the right-hand side insulating body 45 form the second electrode member. The conductive elements 46 and 47 may be any of the small-sized structures recited above, e.g. thin plates, sharp blades, sharp pins or thin wires. The tips 48 and 49 of the conductive elements 46 and 47 are exposed to the reactor channel 43 to serve as active surfaces for generating NRP glow discharges in the air gaps of width d across the reactor channel 43. Note that the inner surfaces 44 of two insulating bodies 45 through which the conductive elements 46 and 47 arise may face each other in parallel as shown or they may be arranged at an angle, e.g. perpendicular to each other. In all cases glow discharges can be obtained in the air gaps between the conductive elements 46 and 47 as long as the air gap dimensions and other relevant parameters are properly set as explained above.

For example, FIG. 23 is a partial perspective view illustrating a parallelepiped insulating body 45 having an internal surface 44 forming one wall of the reactor channel. Thin wires 46 embedded in the insulating body 45 have their tips 48 exposed to the reactor channel through the internal surface 44. Alternatively, the thin wires 46 could be replaced with thin, conductive plates arranged horizontally and mutually spaced in the vertical direction, so that horizontal layers of the insulating body 45 are alternated with the thin plates to form a multilayered structure. Such multilayered structures are manufactured more easily and can be cut-to-size to form any desired shape for the reactor channel wall.

Figure 24:
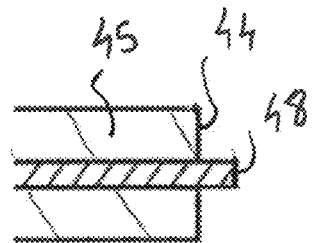
FIGS. 24 to 26 are detailed views showing different positions of a tip portion of the embedded electrode member with respect to the insulating body.
Figure 25:
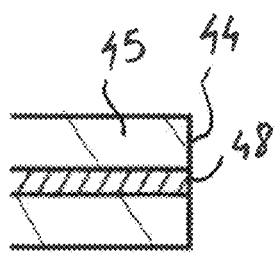
Figure 26:
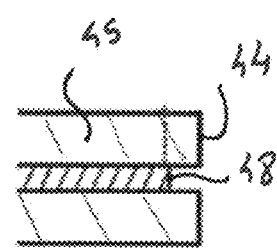

As shown on FIGS. 24 to 26, the tips of the conductive elements may be arranged in different manners with respect to the surface 44 of insulating body 45, i.e. protruding from surface 44 (FIG. 24), flush with surface 44 (FIG. 25), or recessed from surface 44 (FIG. 26).

Figure 27:
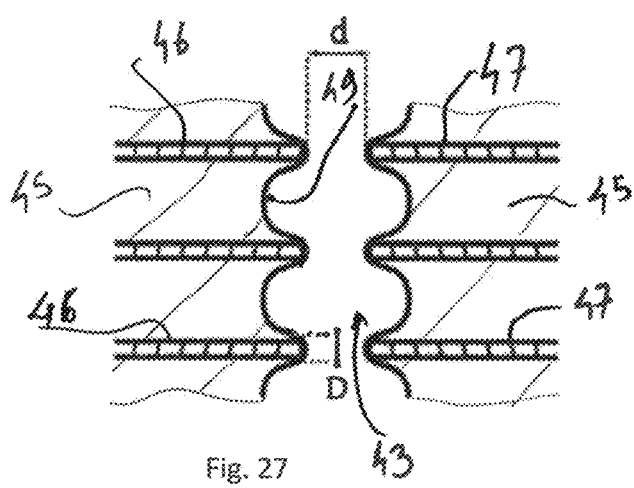
FIG. 27 is a cross-sectional view of a reactor channel defined by the inner surface of an electrically insulating body, in a second embodiment.

By defining the reactor channel 43 within or between insulating bodies, a great diversity of shapes by be formed in the reactor channel walls. For example, FIG. 27 shows a modified embodiment of the reactor channel 23 in which the insulating body 45 are shaped to form bellows or chambers 49 between each successive pair of conductive elements 46, 47. The shaping of the channel walls may be configured to influence the flow of air, e.g. so as to promote thermal diffusion, pressure relaxation or other similar phenomena.

Figure 28:
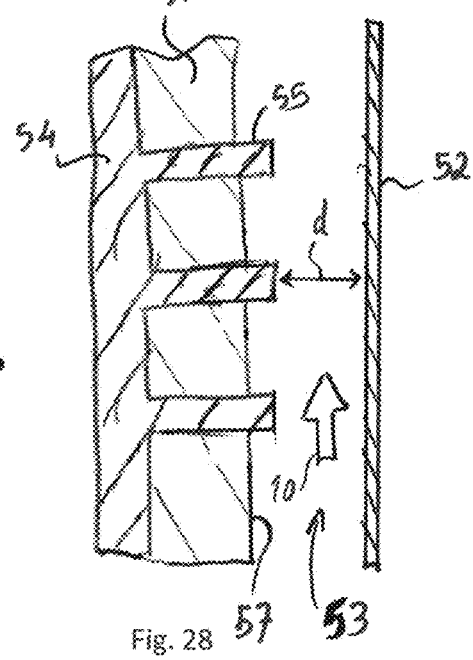
FIG. 28 is a cross-sectional view of a reactor channel suitable for a reactive gas generation apparatus with dissymmetrical electrode members.

FIG. 28 illustrates a reactor channel 53 defined between two dissymmetrical electrode members. Namely, a large, planar conductive sheet 52 arranged parallel to the reactor channel is employed as the electrode member on the right-hand side, whereas the left-hand side electrode member consists of a plurality of small-sized conductive elements SS, e.g. thin plates, sharp blades, sharp pins or thin wires, embedded in an insulating body 56 and having a tip portion exposed to the reactor channel 53 through the inner surface 57 of insulating body 56.

Figure 30:
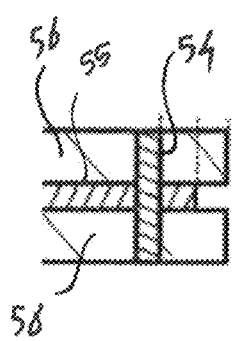
FIGS. 29 to 30 are detailed views showing combinations of a conductive sheet with an electrode member embedded in an insulating body.
Figure 29:
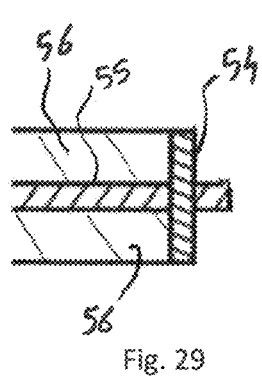

FIGS. 28 to 30 also illustrate various combinations of a plurality of small-sized conductive elements 55 with a conductive sheet 54. As explained, the conductive sheet 54 in the electrode member may help reduce branching of the discharge and/or serve other purposes, e.g. distributing electrical power to the small-sized conductive elements 55. In FIG. 28 the insulating body 56 lies on the side of the conductive sheet 54 turned towards the reactor channel. In FIG. 29 the insulating body 56 lies on the side of the conductive sheet 54 opposite to the reactor channel. In FIG. 30 insulating bodies 56 are arranged on both sides of the conductive sheet 54.

Figure 31:
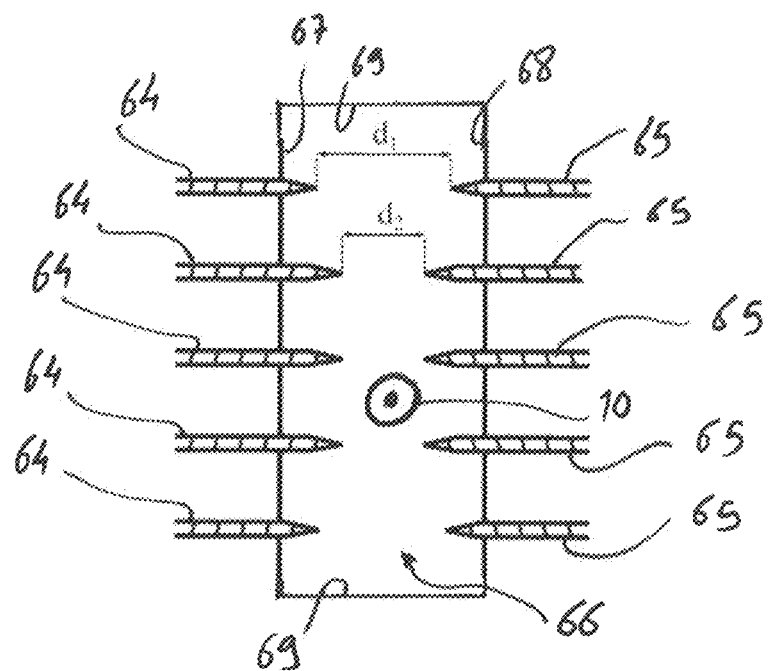
FIG. 31 is a cross-sectional view of a reactor channel in which non-uniform air gaps are made.

In FIG. 31 a reactor channel 66 having a rectangular cross section is shown. The flow of air 10 is perpendicular to the drawing sheet. Conductive pins 64 and conductive pins 65 protrude into reactor channel 66 from opposite walls 67 and 68 and are arranged face to face in pairs to form a plurality of air gaps. The air gaps have variable widths. For example two air gaps located closer to the side walls 69 of reactor channel 66 have a width $d_1$ whereas three air gaps located closer to the center of reactor channel 66 have a width $d_2 < d_1$. The width of the air gaps may be adjusted as a function of properties of the flow, e.g. to influence air flow 10 or to compensate for heterogeneities in air flow 10. For example, the illustrated arrangement makes it possible to increase the density of electric power deposited in the center of the flow where flow speed is higher and to decrease the density of electric power deposited in the side portions of the flow where flow speed is lower. As a consequence, the distribution of temperature across the reactor channel 66 is homogenized.

Figure 32:
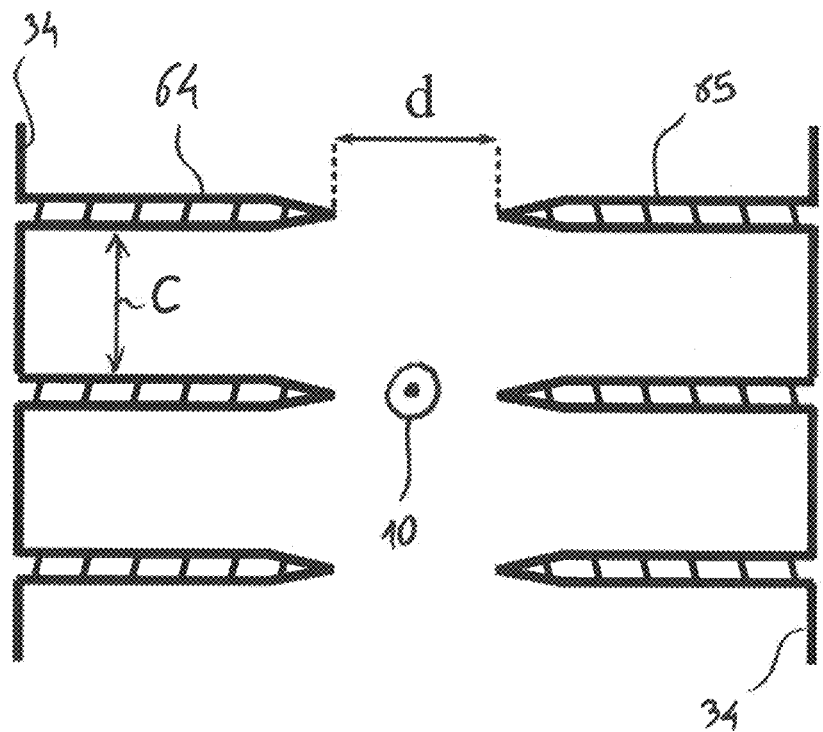
FIG. 32 is a cross-sectional view of a reactor channel in which uniform air gaps are made

FIG. 32 illustrates another arrangement of electrode members similar to FIG. 12. Again, flow of air 10 is perpendicular to the drawing sheet, but the air gaps between conductive pins 64 and conductive pins 65 have identical width. Each electrode member includes a conducting sheet 34. While the individual conductive pins 64 and 65 are arranged at a certain spacing distance C in this figure, it should be noted that such spacing can be configured to any desired value, including C=0 where the conductive pins are in touch side-by-side.

Figure 33:
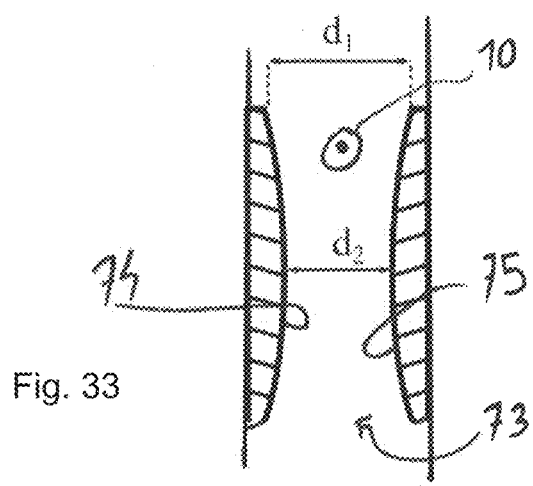
FIG. 33 is a cross-sectional view of a reactor channel in which a variable-width air gap is made.

FIG. 33 illustrates a reactor channel 73 in cross section so that air flow 10 is perpendicular to the drawing sheet. Two planar electrodes 74 and 75, e.g. razor blades, are arranged face to face to define an air gap there-between. The end surface of the electrodes 74 and 75 is convexly curved so that the width of the air gap varies from $d_2$ at the center to $d_1 > d_2$ at the ends of the air gap. Again, this may serve to accommodate constraints of the air flow, e.g. to homogenize temperature.

Figure 34:
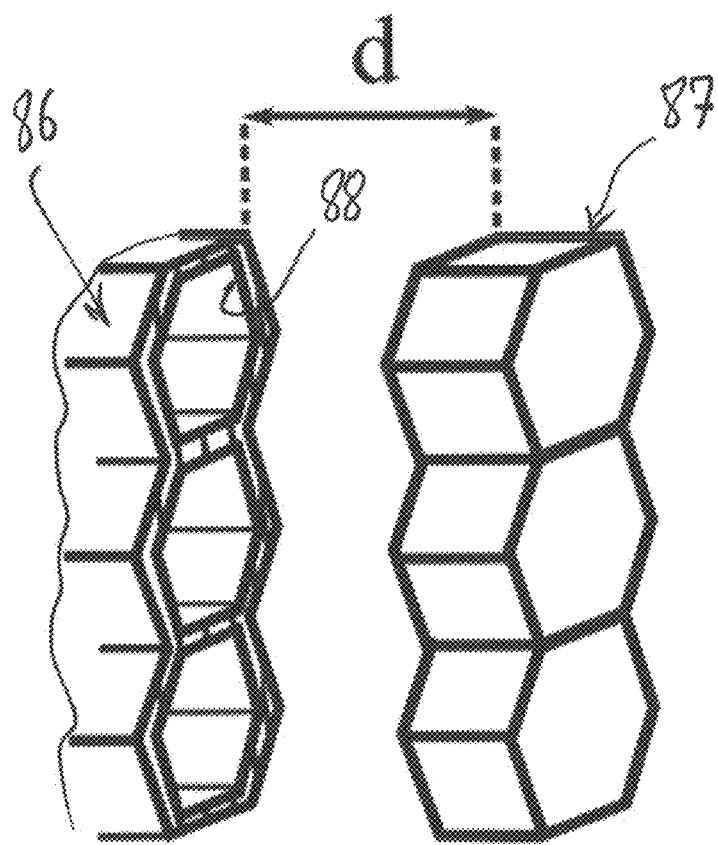
FIG. 34 is a perspective view of electrode members made of honeycomb structures.

FIG. 34 is a perspective view of two honeycomb structures 86 and 87 made in a conductive material and arranged face to face to form two electrode members separated by an air gap with width d. The honeycomb structure consists of thin planar walls 88 arranged in polygonal, e.g. hexagonal lattices. The thickness of planar walls 88 should be a small dimension to promote NRP glow discharges. Namely, the influence of the wall thickness on the glow regime is similar to the influence of osculating circle radius R discussed with reference to FIGS. 3 to 5.

The above described electrode members may be manufactured using Printed-circuit boards (PCBs) since they allow for geometries with the desired features, i.e. conductive structures having a small dimension in at least one direction transverse to the air gap. PCB manufacturing consists of depositing metal onto an insulating plastic board to create any desired circuit geometry.

Figure 35:
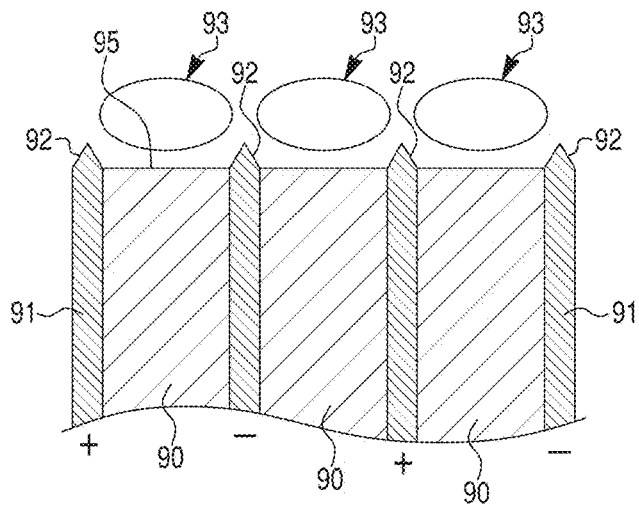
FIGS. 35 to 37 illustrate multilayered structures suitable for generating glow discharges.
Figure 36:
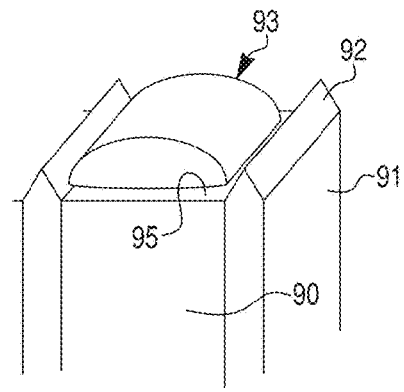

FIGS. 35 and 36 illustrate an embodiment in which both electrode members are integrated into as a single multilayered structure, with alternated dielectric layers 90 and thin conductive plates 91. FIG. 35 is a sectional view and FIG. 36 is a perspective view of the multilayered structure. Adjacent conductive plates 91 are connected to opposite polarities to develop a glow discharge 93 parallel to the inner wall 95 of dielectric layer 90. Namely, by contrast with other embodiments, e.g. FIG. 22, the first and second electrode members are located on a same side of the reactor channel and consist of the thin plates 91 in succession, every two of which belongs to the first electrode member and every other two of which belongs to the second electrode member.

Figure 37:
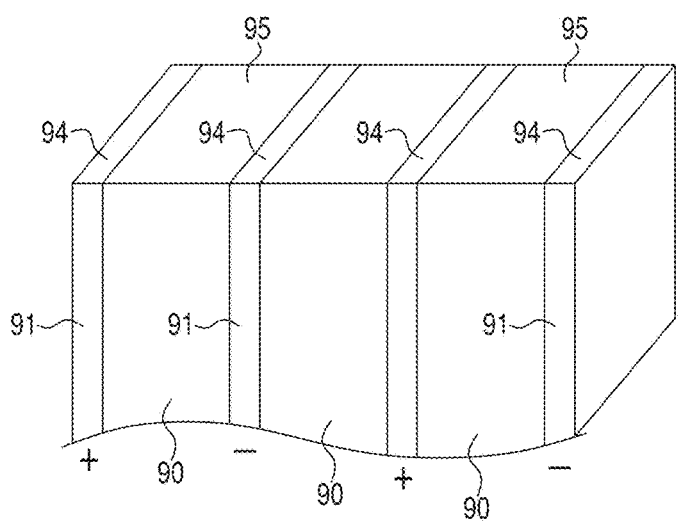

In FIGS. 35 and 36, the thin plate 91 has a sharp edge 92 protruding in the reactor channel. The embodiment of FIG. 37 is similar, except for the flat end surfaces 94 of the thin plates 91 which lie flush with the inner wall 95. In both cases, an air gap is formed between the sharp edges 92 or flat end surfaces 94 of two adjacent thin plates 91, parallel to the inner wall 95.

FIGS. 38 to 41 relate to illustrative electrical setups suitable for superimposing an alternative (ac) or a constant (dc) voltage to high voltage pulses.

Figure 38:
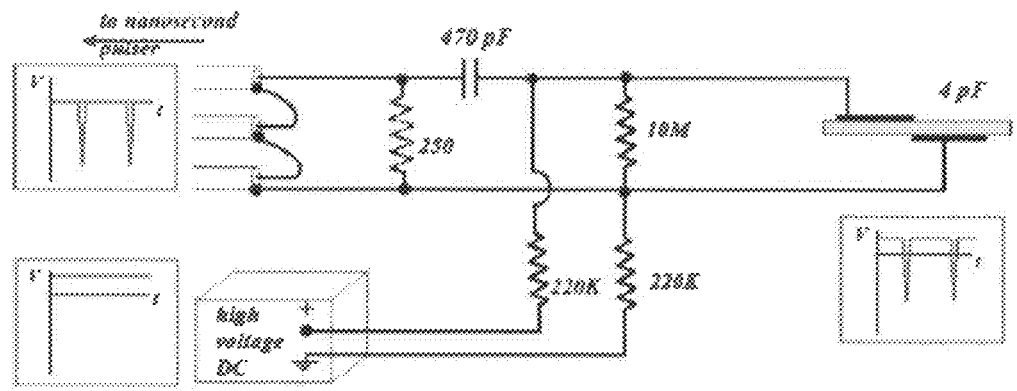
FIG. 38 is a functional view of an electrical setup suitable for superimposing a DC voltage to high voltage pulses.
Figure 39:
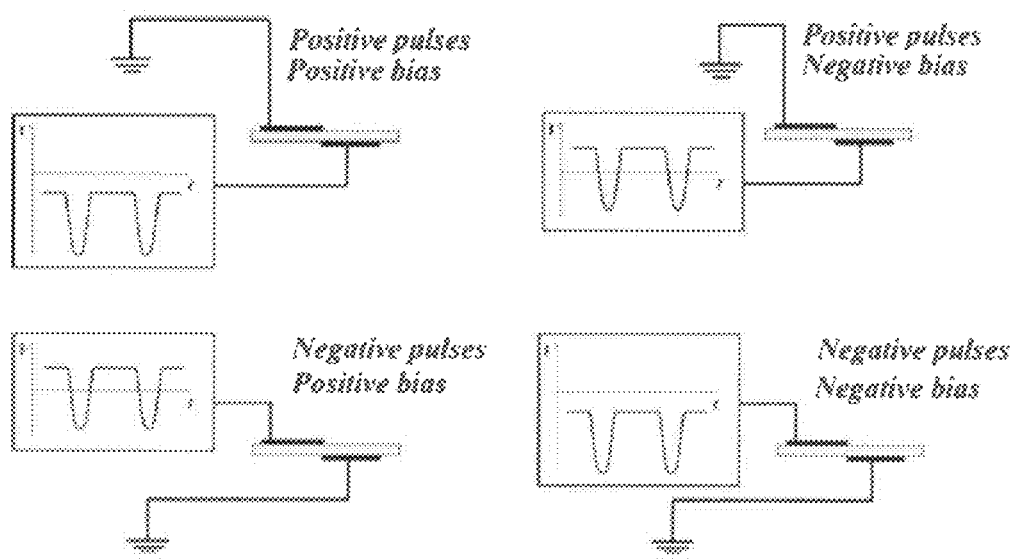
FIG. 39 is a diagram that illustrates resulting combinations of pulse and bias voltage.

In FIG. 38, the illustrated electric circuit serves to combine short pulses with a low frequency bias voltage. The resulting combinations of pulse and bias voltage are shown in FIG. 39. The circuit is designed so as to combine short pulses with a low frequency bias voltage without interference between the pulser and the low frequency power supply. Adding a capacitor in series with the actuator shields the pulser from the bias voltage. In experiments with sinusoidal bias, the dc power supply may be replaced by a high-voltage transformer.

Adding a 470 pF capacitor in series with the actuator shields the pulser from the bias voltage. Since the capacitance of the actuator is only 4 pF, the main voltage drop occurs just at the plasma actuator. The 220 kΩ_ resistor do not let the pulse go to the power supply. The charging time for the capacitor through the corresponding resistors is _RC=220 kΩ_x 470 pF=_100 μs, which corresponds to 10 kHz>>_60 Hz. The 10 MΩ_ resistor is put in parallel with the actuator for safety reasons. It discharges the high-voltage electrode after experiments. Its high impedance does not influence the circuit in any way. Also, a non-inductive 250Ω resistor is added in parallel with the actuator to minimize the pulse reflection.

The pulser used in FIG. 38 is a FID Technology 4 ns full width at half maximum _(FWHM)_ pulser capable of running with pulse repetition rate _(PRR)_ of up to 100 KHz and triggered by a _10 V pulse from a Stanford Box. The peak output voltage of the pulser is up to 10 kV which is fed to three separate 3 m long 75_Ω coaxial lines. The three copropagating pulses are converted into a single pulse by taking advantage of the short physical "length" of the pulses _(less than 1 m)_. By connecting the center conductor of the first coaxial line to the outer conductor of the second and the center conductor of the second to the outer conductor of the third, an amplified pulse is produced between the center conductor of the third line and the outer conductor of the first. This essentially is a transformer made of sections of transmission lines, and it is well described in the literature.

A source of constant bias voltage used in FIG. 38 is High Voltage DC Supply model 412 by John Fluke MFG Co. Inc., capable of producing output voltages up to 2 kV both polarities. Ozone generator transformer by Plasma Technics, Inc. is used for producing sinusoidal bias voltage. The pulser is able to produce pulses of negative polarity only. The bias voltage could be of any polarity.

In FIG. 39, the encapsulated electrode is always considered to be at zero potential. The sign of potential of the exposed electrode relative to the encapsulated one determines the pulse and bias polarity.

Figure 40:
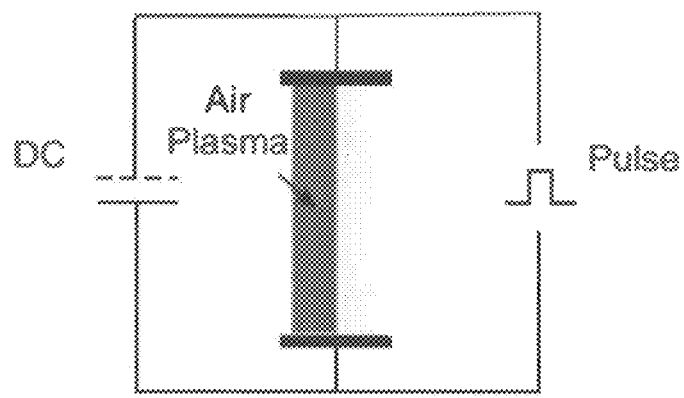
FIGS. 40 and 41 are functional views of other electrical setups suitable for superimposing a DC voltage to high voltage pulses.

Another schematic of a combined pulsed and DC discharge arranged in parallel is illustrated in FIG. 40. The circuit schematic is shown in FIG. 40. For example, with a DC voltage of 2 kV and current of 150 mA, the electron density does not decrease below $6.5 \times 10^{11}$ cm$^{-3}$, which makes it easier for the pulses (here 10 kV, 10 ns) to increase the electron density, and this is envisioned to produce more active species.

Figure 41:
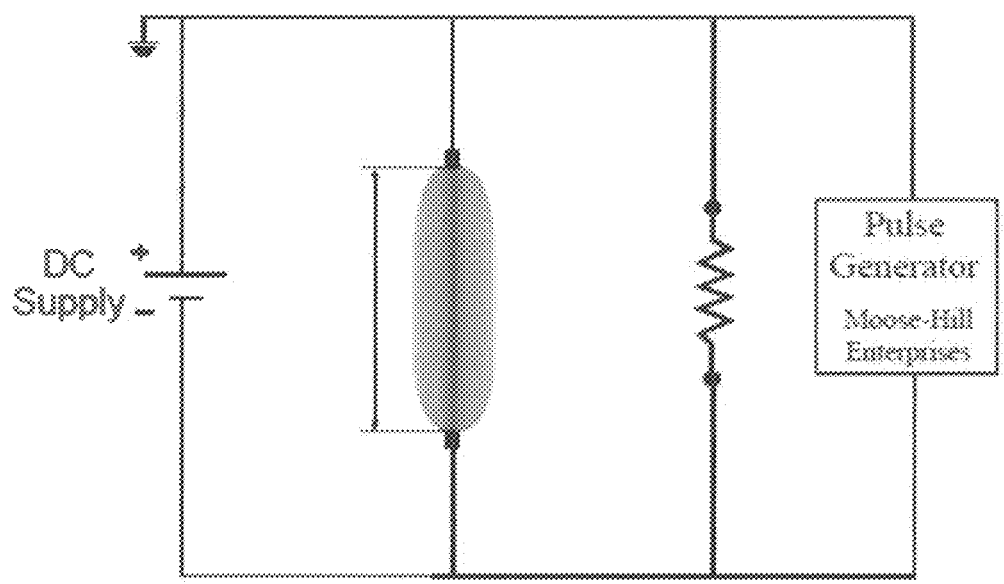

In the repetitive pulse discharge circuit schematic shown on FIG. 41, the DC circuit is applied only for conductivity measurements. A repetitive pulser capable of generating 10 ns pulses, with peak voltages of 3-12 kV and pulse repetition frequencies up to 100 kHz is provided by Moose-Hill/FID Technologies. This pulser operates with a solid-state opening switch or Drift-Step Recovery Diode (DSRD). The experimental set-up is shown in FIG. 41. The DC circuit in parallel with the pulser was used only to determine the electron number density from the plasma conductivity. This arrangement can be used also to enhance the electron number density, hence the density of active species, as described in reference to FIG. 40.

The reactive gas generated by the above described apparatuses may be employed for other purposes than decontamination, e.g., surface treatment such as surface priming in industrial environments. Surface priming as employed herein refers to altering the charge or chemical composition of surfaces for the purpose of modifying surface properties in preparation for subsequent processes, e.g., industrial gluing processes, wetting processes, etc. Further applications include the treatment of dermatological diseases such as mycosis, psoriasis and enancters and the treatment of carcinoma.

The invention is not limited to the described embodiments. The appended claims are to be construed as embodying all modification and alternative constructions that may be occurred to one skilled in the art, which fairly fall within the basic teaching here, set forth.

The use of the verb "to comprise" or "to include" and its conjugations does not exclude the presence of elements or steps other than those stated in a claim. Furthermore, the use of the article "a" or "an" preceding an element or step does not exclude the presence of a plurality of such elements or steps.

The invention claimed is:

1. An apparatus for generating a flow of reactive gas, comprising:
    a reactor channel for receiving an incoming flow of air,
    first and second electrode members made of an electrically conductive material, each of the first and second electrode members having at least one active surface exposed to the reactor channel, wherein the at least one active surface of the first electrode member and the at least one active surface of the second electrode member are arranged in spaced relationship to define an air gap there-between in the reactor channel,
    wherein the at least one active surface of the first electrode member is turned towards the second electrode member, so that the air gap is formed between each of the at least one active surface of the first electrode member and the at least one active surface of the second electrode member, wherein each active surface of the first electrode member has a dimension lower than 2 mm in at least one direction transverse to the air gap, and
    an electric pulse generator configured to repetitively generate voltage pulses between the first and second electrode members so as to produce glow discharges in the air gap between the at least one active surface of the first electrode member and the at least one active surface of the second electrode member, the voltage pulses being generated at time intervals less than 1 millisecond and the voltage pulse duration being less than about 500 ns, the glow discharges being adapted to transform part of the incoming flow of air into reactive gas at a delivery temperature, wherein a difference between the delivery temperature of the reactive gas and a temperature of the incoming flow of air is no more than 200 K, wherein the reactive gas comprises free radicals and molecules and atoms in electronic excited states.

2. The apparatus of claim 1, wherein the first electrode member comprises a first plurality of conductive elements extending towards the second electrode member, wherein a plurality of active surfaces of the first electrode member are provided at a tip of each conductive element turned towards the second electrode member.

3. The apparatus of claim 2, wherein the conductive elements extending towards the second electrode member are selected from the group consisting of thin plates having a thickness lower than 2 mm, sharp blades having a radius of curvature at the tip lower than 2 mm, thin wires having a radius lower than 2 mm, and sharp pins having a radius of curvature at the tip lower than 2 mm.

4. The apparatus of claim 2, wherein the conductive elements of the first electrode member are spaced along at least one direction transverse to the air gaps.

5. The apparatus of claim 2, further comprising an electrically insulating body having an inner surface defining the reactor channel for receiving the incoming flow of air, wherein at least one of the conductive elements of the first electrode member has a base portion embedded in the electrically insulating body and a tip portion exposed to the reactor channel.

6. The apparatus of claim 5, wherein the conductive elements are selected from the group consisting of thin plates and sharp blades and wherein the conductive elements are arranged in layers in a first direction and mutually spaced in a second direction, the second direction being different from the first direction, so that the insulating body is alternated with the conductive elements to form a multilayer structure, wherein the tip portion of the conductive elements of the first electrode member is one of protruding from, flush with and recessed relative to the inner surface of the electrically insulating body.

7. The apparatus of claim 2, wherein the first electrode member further comprises a conductive sheet arranged parallel to the reactor channel and wherein the first plurality of conductive elements protrudes from a surface of the first conductive sheet into the reactor channel.

8. The apparatus of claim 7, wherein the second electrode member further comprises a second conductive sheet arranged parallel to the first conductive sheet.

9. The apparatus of claim 7, wherein a distance between the conductive sheet of the first electrode member and a tip of the conductive elements protruding from the conductive sheet is less than about 4 mm.

10. The apparatus of claim 2, wherein the second electrode member comprises a second plurality of active surfaces turned towards the first electrode member, so as to form said air gaps between the first plurality of active surfaces and the second plurality of active surfaces, wherein each active surface of the second electrode member has a dimension lower than 2 mm.

11. The apparatus of claim 10, wherein the active surfaces of the first electrode member and the active surfaces of the second electrode member are arranged at corresponding positions so as to form a plurality of pairs of active surfaces each pair comprising a first active surface of the first electrode member and a second active surface of the second electrode member and an identical air gap between the first and second active surfaces.

12. The apparatus of claim 11, wherein a width of the air gap between the active surfaces of the first and second electrode members is between about 1 and 100 mm.

13. The apparatus of claim 12, wherein the width of the air gap between the active surfaces of the first and second electrode members is between about 2 mm and about 20 mm.

14. The apparatus of claim 2, wherein the conductive elements extending towards the second electrode member are selected from the group consisting of thin plates having a thickness lower than 500 μm, sharp blades having a radius of curvature at the tip lower than 500 μm, thin wires having a radius lower than 500 μm, and sharp pins having a radius of curvature at the tip lower than 500 μm.

15. The apparatus of claim 1, wherein the first electrode member comprises thin wire, wherein a radius of said thin wire is lower than 2 mm.

16. The apparatus of claim 1, wherein the second electrode member comprises an active surface of large dimensions forming air gaps with each active surface of the first electrode member.

17. The apparatus of claim 1, further comprising:
an air blower for generating the incoming flow of air through the reactor channel, and
an output section for delivering the reactive gas from the reactor channel to a sample or region to be treated.

18. The apparatus of claim 17, further comprising a hollow envelope made of an electrically insulating material, the hollow envelope having a tubular shape with a first open end connected to the air blower and a second open end connected to the output section of the apparatus, wherein the first electrode member and second electrode member are arranged on inner surfaces of the hollow envelope, wherein the reactor channel is defined within the hollow envelope.

19. The apparatus of claim 17, wherein the air blower has an input connected to an atmosphere for sucking ambient air and an end connected to the reactor channel for blowing the flow of air into the reactor channel.

20. The apparatus of claim 1, wherein the electric pulse generator is configured to generate the voltage pulses at a pulse repetition frequency between 5 kHz and 500 kHz.

21. The apparatus of claim 1, wherein an amplitude of a voltage pulse is between about 1 kV and about 50 kV.

22. The apparatus of claim 21, wherein the amplitude of the voltage pulse is between about 5 kV and about 30 kV.

23. The apparatus of claim 1, further comprising a length of coaxial cable connecting the electric pulse generator to at least one of the electrode members.

24. The apparatus of claim 1, wherein the first electrode member is connected to the electric pulse generator and the second electrode members is connected to an electrical ground potential.

25. The apparatus of claim 1, wherein the reactive gas has a decontaminating or sterilizing effect.

26. The apparatus of claim 1, wherein the electric pulse generator is configured to generate the voltage pulses superimposed on a static or alternating voltage.

27. The apparatus of claim 26, wherein the electric pulse generator is configured to generate the voltage pulses and/or the static or alternating voltage in burst mode.

28. A method for generating a flow of reactive gas, comprising:
receiving an incoming flow of air in a reactor channel,
providing first and second electrode members made of an electrically conductive material, each of the first and second electrode members having at least one active surface exposed to the reactor channel, wherein the at least one active surface of the first electrode member and the at least one active surface of the second electrode member are arranged in spaced relationship to define an air gap there-between in the reactor channel, wherein the at least one active surface of the first electrode member is turned towards the second electrode member, so that the air gap is formed between each of the at least one active surface of the first electrode member and the at least one active surface of the second electrode member, wherein each active surface of the first electrode member has a dimension lower than 2 mm in at least one direction transverse to the air gap, and repetitively generating voltage pulses between the first and second electrode members so as to produce glow discharges in the air gap between the at least one active surface of the first electrode member and the at least one active surface of the second electrode member, the voltage pulses being generated at intervals less than 1 millisecond and voltage pulse duration less than about 500 ns, the glow discharges being adapted to transform part of the incoming flow of air into reactive gas at a delivery temperature, wherein a difference between the delivery temperature of the reactive gas and a temperature of the incoming flow of air is no more than 200 K, wherein the reactive gas comprises free radicals, ions, and molecules and atoms in electronic excited states.

29. The method of claim 28, further comprising:
    delivering the reactive gas from the reactor channel to a sample or region to be treated.

30. The method of claim 29, wherein a temperature difference between the reactive gas delivered from the reactor channel and an ambient atmosphere is lower than 50 K.

31. The method of claim 29, wherein the reactive gas decontaminates the treated sample or region.

32. The method of claim 29, wherein the reactive gas provides chemical surface treatment of the treated sample or region.

* * * * *